US012559852B2

United States Patent
(12) United States Patent
Arnold et al.

(10) Patent No.: US 12,559,852 B2
(45) Date of Patent: Feb. 24, 2026

(54) COMPOSITION FOR TIN-SILVER ALLOY ELECTROPLATING COMPRISING A COMPLEXING AGENT

(71) Applicant: BASF SE, Ludwigshafen am Rhein (DE)

(72) Inventors: Marco Arnold, Ludwigshafen (DE); Alexander Fluegel, Ludwigshafen (DE); Elisabeth Kuttner, Ludwigshafen am Rhein (DE); Doris Kremzow-Graw, Ludwigshafen am Rhein (DE); Nadine Engelhardt, Ludwigshafen am Rhein (DE); Johannes Kaschel, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 125 days.

(21) Appl. No.: 17/753,653

(22) PCT Filed: Sep. 8, 2020

(86) PCT No.: PCT/EP2020/075080
§ 371 (c)(1),
(2) Date: Mar. 10, 2022

(87) PCT Pub. No.: WO2021/052817
PCT Pub. Date: Mar. 25, 2021

(65) Prior Publication Data
US 2024/0060201 A1 Feb. 22, 2024

(30) Foreign Application Priority Data
Sep. 16, 2019 (EP) .................................... 19197517

(51) Int. Cl.
*C25D 3/60* (2006.01)
*C07C 321/20* (2006.01)
(Continued)

(52) U.S. Cl.
CPC ............. *C25D 3/32* (2013.01); *C07C 321/20* (2013.01); *C07C 335/18* (2013.01);
(Continued)

(58) Field of Classification Search
CPC ............... C25D 3/60; C25D 3/64; C25D 5/02
(Continued)

(56) References Cited

U.S. PATENT DOCUMENTS 6,607,653 B1 8/2003 Tsuji et al.
11,926,918 B2 3/2024 Kienle et al.
(Continued)

FOREIGN PATENT DOCUMENTS

EP 0144990 A2 6/1985
EP 0166347 A2 1/1986
(Continued)

OTHER PUBLICATIONS

Non-Final Rejection from U.S. Appl. No. 17/040,642 dated Dec. 13, 2023. (Year: 2023).*
(Continued)

*Primary Examiner* — Edna Wong
(74) *Attorney, Agent, or Firm* — Armstrong Teasdale LLP

(57) ABSTRACT

An aqueous composition including (a) metal ions including tin ions and silver ions and (b) at least one complexing agent of formula C11

$$R^{C12}\text{-}X^{C11}\text{-}R^{C11} \quad \text{(C11)}$$

(Continued)

and their salts, where $X^{C11}$ is selected from (a) a divalent 5 or 6 membered aromatic N-heterocyclic group;

(b) a divalent 6 membered aromatic carbocyclic group; and (c) a divalent 5 or 6 membered aliphatic N-heterocyclic group including one N atom and optionally a second heteroatom selected from N and O;

all of which may be unsubstituted or substituted by one or more OH or one or more $R^{C14}$;

$R^{C11}$ is selected from (a)

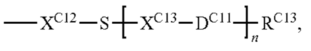

(b)

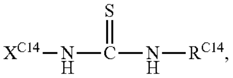

and (c)

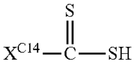

; and $R^{C12}$ is selected from $R^{C11}$, $X^{C11}$-$R^{C11}$, H, OH, $NR^{C14}_2$, $C_1$ to $C_{10}$ alkyl, and $C_1$ to $C_{10}$ alkoxy

14 Claims, 2 Drawing Sheets

(51) Int. Cl.

| | |
|---|---|
| ***C07C 335/18*** | (2006.01) |
| ***C07D 213/32*** | (2006.01) |
| ***C07D 233/60*** | (2006.01) |
| ***C07D 277/26*** | (2006.01) |
| ***C25D 3/32*** | (2006.01) |
| ***C25D 3/64*** | (2006.01) |
| ***C25D 5/02*** | (2006.01) |

(52) U.S. Cl.
CPC ......... *C07D 213/32* (2013.01); *C07D 233/60* (2013.01); *C07D 277/26* (2013.01); *C25D 3/64* (2013.01)

(58) Field of Classification Search
USPC ......................... 205/238, 253, 118, 123, 125
See application file for complete search history.

(56) References Cited

U.S. PATENT DOCUMENTS

| | | | | |
|---|---|---|---|---|
| 12,054,842 | B2 * | 8/2024 | Fritzsche | C07D 417/14 |
| 2007/0037377 | A1 | 2/2007 | Richardson et al. | |
| 2009/0237769 | A1 * | 9/2009 | Hakii | G02B 5/0242 359/270 |
| 2012/0138471 | A1 | 6/2012 | Mayer et al. | |
| 2016/0122460 | A1 * | 5/2016 | Fedurco | C09J 175/04 428/626 |
| 2019/0127871 | A1 | 5/2019 | Chiang et al. | |
| 2019/0368063 | A1 | 12/2019 | Yamaguchi et al. | |
| 2021/0025070 | A1 * | 1/2021 | Fritzsche | C07D 401/14 |
| 2021/0140060 | A1 * | 5/2021 | Tatsumi | C25D 7/00 |

FOREIGN PATENT DOCUMENTS

| | | | | |
|---|---|---|---|---|
| EP | 2626449 | A2 | 8/2013 | |
| JP | 11269691 | A * | 10/1999 | C25D 3/46 |
| JP | H11269691 | A | 10/1999 | |
| JP | 2006206946 | A * | 8/2006 | C23C 18/42 |
| JP | 2006265573 | A | 10/2006 | |
| JP | 2007218952 | A | 8/2007 | |
| JP | 201731447 | A | 2/2017 | |
| JP | 2019137896 | A | 8/2019 | |
| WO | WO-2018122058 | A1 * | 7/2018 | C23C 18/1658 |
| WO | 2019185468 | A1 | 10/2019 | |

OTHER PUBLICATIONS

Zheng et al., “Tuning the Framework Formation of Silver (I) Coordination Architectures with Heterocyclic Thioethers,” Dalton Transactions (2003), vol. pp. 1509-1514. (Year: 2003).*

International Search Report and Written Opinion for corresponding PCT/EP2020/075080 mailed Feb. 1, 2021; 17 pages.

* cited by examiner

COMPOSITION FOR TIN-SILVER ALLOY ELECTROPLATING COMPRISING A COMPLEXING AGENT

CROSS-REFERENCE TO RELATED APPLICATIONS

This application is a U.S. National Phase Application of International Patent Application No. PCT/EP2020/075080, filed Sep. 8, 2020, which claims priority to European Patent Application No. 19197517.6, filed Sep. 16, 2019, each of which is hereby incorporated by reference herein.

BACKGROUND OF THE INVENTION

The invention relates to tin-silver alloy electroplating compositions comprising a complexing agent, their use and processes for tin-silver alloy electroplating.

Metals and metal-alloys are commercially important, particularly in the electronics industry where they are often used as electrical contacts, final finishes and solders. Lead-free solders, such as tin, tin-silver, tin-copper, tin-bismuth, tin-silver-copper, and others, are common metals used in solders. These solders are often deposited on semiconductor substrates by means of metal electroplating baths.

Certain applications for lead-free solder plating present challenges in the electronics industry. For example, when used as a capping layer on copper pillars, a relatively small amount of lead-free solder, such as tin or tin-silver solder, is deposited on top of a copper pillar.

A typical tin-silver plating solution comprises dissolved tin and silver ions, water, an acid electrolyte such as sulfuric acid or methane sulfonic acid in an amount sufficient to impart conductivity to the bath, an antioxidant, and proprietary additives to improve the uniformity of the plating and the quality of the metal deposit in terms of surface roughness, coplanarity and void formation. Such additives usually include complexing agents that are capable of forming a complex with silver in order to allow silver to be (a) stable in the solution in combination with tin, and (b) deposited in parallel to the less noble tin.

JP 2007218952 A, EP 166347 A, EP 144990 A disclose photographic films which comprise silver compounds and a sulfur containing compound comprising nitrogen containing ring system substituents like 1,8-Bis(2-pyridyl)-3,6-dithiaoctane or 1,11-Bis(2-pyridyl)-3,6,9-trithiaundecane.

JP 2006206946 A discloses silver plating bath comprising, among others, compounds of formula $R_a—S—(CH_2—CH_2—S)_n—R_b$. The bath may be used for depositing silver on printed circuit boards, semiconductor integrated circuits, resistors, variable resistors, capacitors, filters, inductors, thermistors, crystal oscillators, switches, wire and other electronic components.

U.S. Pat. No. 6,607,653 B1 discloses a composition for depositing a tin-copper, a tin-copper-bismuth, or a tin-copper-silver alloy that comprises a specific sulfur containing compound. One of several dozens of compounds could be 1,10-di(2-pyridyl)-1,4,7,10-tetrathiadecane.

US 2012/138471 A1 and EP 2 626 449 A2 disclose tin-silver alloy electroplating compositions comprising N-heterocyclic thiol complexing agents like mercaptopyridine.

WO 2019/185468 discloses tin-silver alloy electroplating compositions comprising a complexing agent, their use and processes for tin-silver alloy electroplating. The complexing agent comprises at least two sulfur atoms which are separated by at least a spacer group $X^{21}$ and which are terminated by 5 or 6 membered aromatic N-heterocyclic group comprising one or two N atoms, again separated by spacer groups $X^1$ and $X^3$.

It is an object of the present invention to provide a tin-silver electroplating composition that is stable over a long time without showing significant deterioration or aging, e.g. by strong coloring or generating deposits and that is capable of electrodepositing tin-silver alloys on semiconductor substrates.

SUMMARY OF THE INVENTION

The present invention provides an aqueous composition comprising (a) metal ions comprising tin ions and silver ions and (b) at least one complexing agent of formula C11

$$R^{C12}\text{-}X^{C11}\text{-}R^{C11} \quad (C11)$$

and their salts, wherein $X^{C11}$ is selected from

- (a) a divalent 5 or 6 membered aromatic N-heterocyclic group comprising
  - (i) a single N atom; or
  - (ii) a first N atom and a second heteroatom selected from N and S, wherein the first N atom and the second heteroatom are separated by at least one C atom; or
  - (iii) a triazole or thiadiazole;
- (b) a divalent 6 membered aromatic carbocyclic group;
- (c) a divalent 5 or 6 membered aliphatic N-heterocyclic group comprising one N atom and optionally a second heteroatom selected from N and O;

all of which may be unsubstituted or substituted by one or more OH or one or more $R^{C14}$;

$R^{C11}$ is selected from (a)

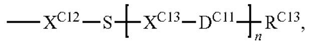

(b)

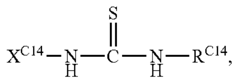

and (c)

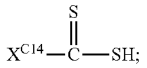

$R^{C12}$ is selected from $R^{C11}$, $X^{c11}$-$R^{C11}$, H, OH, $NR^{C14}_2$, $C_1$ to $C_{10}$ alkyl, and $C_1$ to $C_{10}$ alkoxy;

$X^{C12}$ is a chemical bond or a linear, branched or cyclic $C_1$-$C_6$ alkanediyl, which may be unsubstituted or substituted by OH, with the proviso that if $X^{C11}$ is (a) a divalent 5 or 6 membered aromatic N-heterocyclic group and (b) $R^{C13}$ is substituted by one OH and (c) $R^{C12}$ is not $R^{C11}$, then $X^{C12}$ is a chemical bond;

$X^{C13}$ is a linear, branched or cyclic $C_1$-$C_6$ alkanediyl, which may be unsubstituted or substituted by OH;

$X^{C14}$ is a chemical bond or a linear or branched $C_1$-$C_4$ alkanediyl;

$D^{C11}$ is selected from S and O;

$R^{C13}$ is selected from (a) a linear, branched or cyclic $C_1$-$C_6$ alkyl, which may be unsubstituted or substituted by one or more OH, (b) if $X^{C11}$ is not an aromatic carbocyclic group, Ph, $X^{C14}$-Ph, with Ph=phenyl, and (c) a $C_2$ to $C_4$ polyoxyalkylene group;

with the proviso that if $X^{C11}$ is a divalent 5 or 6 membered aromatic N-heterocyclic group, then $R^{C13}$ is unsubstituted or substituted by one OH with the exception that if $X^{C11}$ is a divalent 5 or 6 membered aromatic N-heterocyclic group comprising a first N atom and a second heteroatom selected from N, then $R^{C13}$ is unsubstituted.

$R^{C14}$ is selected from H and a linear, branched or cyclic $C_1$-$C_6$ alkyl;

n is 0 or an integer of from 1 to 5.

With the aid of the complexing agents the plating baths are stable over a long time without showing coloring or deposits and are capable of electrodepositing tin-silver alloys on semiconductor substrates, particularly tin-silver alloy solder bumps.

The invention further relates to the use of a tin-silver alloy plating bath comprising a composition as defined herein for depositing tin-silver alloys on a substrate comprising features having an aperture size of 500 nm to 500 μm.

The invention further relates to a process for depositing a tin-silver alloy layer on a substrate by a) contacting a composition as defined herein with the substrate, and b) applying a current to the substrate for a time sufficient to deposit a tin or tin alloy layer onto the substrate, wherein the substrate comprises features having an aperture size of 500 nm to 500 pm and the deposition is performed to fill these features.

The invention further relates to complexing agents selected from: 3-[2-(2,3-dihydroxypropylsulfanyl)phenyl]sulfanylpropane-1,2-diol; 3-[2-(2,3-dihydroxypropylsulfanyl)-4-methyl-phenyl]sulfanylpropane-1,2-diol; 3-[[2-(2,3-dihydroxypropylsulfanylmethyl)phenyl]methylsulfanyl]propane-1,2-diol; 2,6-bis(2-ethylsulfanylethylsulfanylmethyl)pyridine; morpholine-4-carbodithioate tetramethylammonium salt; piperazine-1,4-dicarbodithioate ditetramethylammonium salt; 3-[[3-(2,3-dihydroxypropylsulfanylmethyl)phenyl]methylsulfanyl]propane-1,2-diol; 2-[2-(2-propylsulfanylethylsulfanyl)ethyl]pyridine; 2-[2-(2-methylsulfanylethylsulfanyl)ethyl]pyridine; 2-(2-ethylsulfanylethylsulfanylmethyl)-6-[6-(2-ethylsulfanylethylsulfanylmethyl)-2-pyridyl]pyridine; 2,6-bis(2-methylsulfanylethylsulfanylmethyl)pyridine; 4-[2-(2-ethylsulfanylethylsulfanyl)ethyl]-morpholine; 2-[2-(2-isopropylsulfanylethylsulfanyl)ethyl]pyridine; 2-(2-propylsulfanylethylsulfanylmethyl)pyridine; 2-[2-(2-ethylsulfanylethylsulfanyl)-1-methyl-ethyl]thiazole; 2-[2-(2-benzylsulfanylethylsulfanyl)ethyl]pyridine; and 2-[2-(2-phenylsulfanylethylsulfanyl)ethyl]pyridine; and their salts.

DETAILED DESCRIPTION OF THE INVENTION

Complexing Agents According to the Invention

Figure 1:
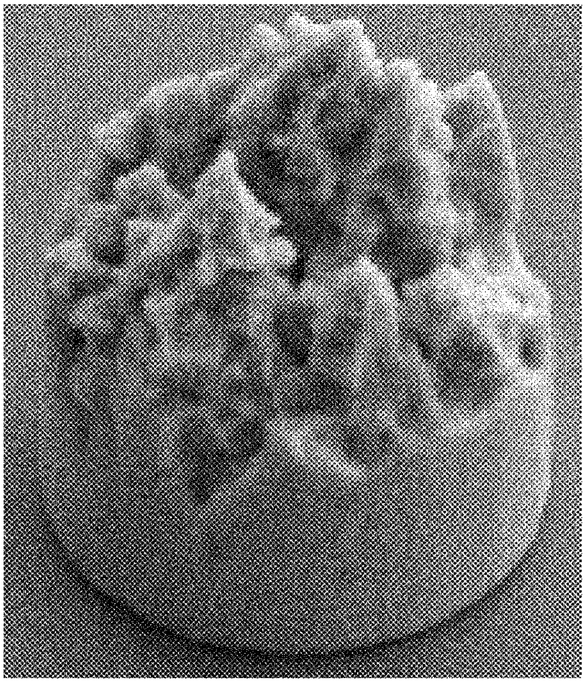
FIG. 1 shows a SEM image of a tin bump electroplated according to Comparative Example 3.1.
Figure 2:
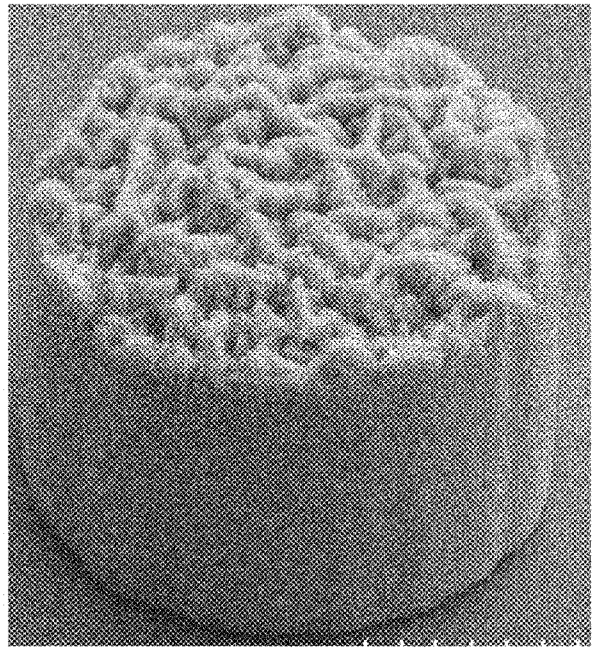
FIG. 2 shows a SEM image of a tin bump electroplated according to Example 3.2.
Figure 3:
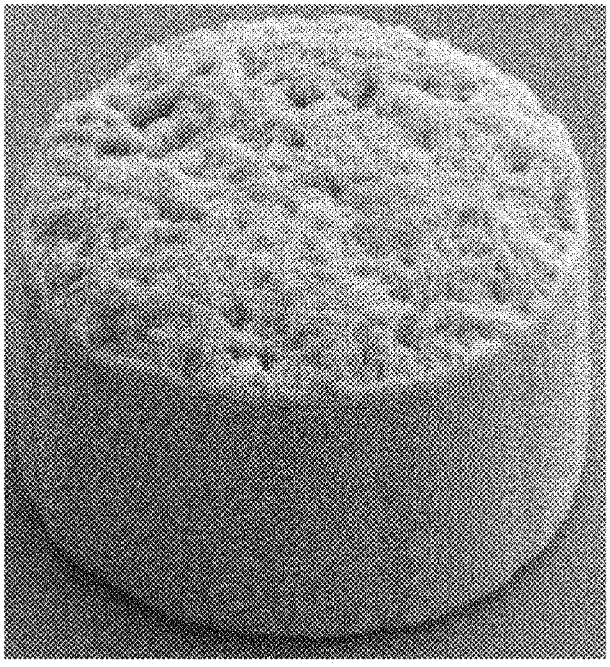
FIG. 3 shows a SEM image of a tin bump electroplated according to Example 3.3.

It was found that compositions for tin-silver alloy electroplating according to the invention comprising at least one complexing agent as described below are stable over a long time without showing coloring or deposits and are capable of electrodepositing tin-silver alloys on semiconductor substrates, particularly tin-silver alloy solder bumps. Long time stability here means a stable bath over a period of at least 6 months.

Besides tin ions and silver ions the aqueous compositions, preferably aqueous solutions, according to the present invention comprises at least one complexing agent compound of formula C11

$$R^{C12}\text{-}X^{C11}\text{-}R^{C11} \quad (C11)$$

and their salts.

In formula C11

$X^{C11}$ is selected from (a) a divalent 5 or 6 membered aromatic N-heterocyclic group comprising (i) a single N atom; or (ii) a first N atom and a second heteroatom selected from N and S, wherein the first N atom and the second heteroatom are separated by at least one C atom; or (iii) a triazole or a thiadiazole;

(b) a divalent 6 membered aromatic carbocyclic group;

(c) a divalent 5 or 6 membered aliphatic N-heterocyclic group comprising a first N atom and optionally a second heteroatom selected from N and O;

all of which may be unsubstituted or substituted by one or more OH or one or more $R^{C14}$;

$R^{C11}$ is selected from $$-X^{C12}-S-\left[X^{C13}-D^{C11}\right]_n-R^{C13}, \quad (a)$$

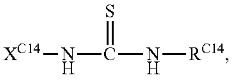 (b)

and

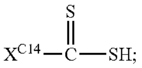 (c)

$R^{C12}$ is selected from $R^{C11}$, $X^{11}$-$R^{C11}$, H, OH, $NR^{C14}_2$, $C_1$ to $C_{10}$ alkyl, and $C_1$ to $C_{10}$ alkoxy;

$X^{C12}$ is a chemical bond or a linear, branched or cyclic $C_1$-$C_6$ alkanediyl, which may be unsubstituted or substituted by OH, with the proviso that if $X^{C11}$ is (a) a divalent 5 or 6 membered aromatic N-heterocyclic group, (b) $R^{C13}$ is substituted by one OH and (c) $R^{C12}$ is not $R^{C11}$, then $X^{C12}$ is a chemical bond;

$X^{C13}$ is a linear, branched or cyclic $C_1$-$C_6$ alkanediyl, preferably a linear or branched $C_1$ to $C_4$ alkanediyl, which may be unsubstituted or substituted by OH, preferably unsubstituted;

$X^{C14}$ is a chemical bond or a linear or branched $C_1$-$C_4$ alkanediyl, preferably a chemical bond, methanediyl, ethanediyl, 1,2- or 1,3-propanediyl;

$D^{C11}$ is selected from S and O, preferably S;

$R^{C13}$ is selected from (a) a linear, branched or cyclic $C_1$-$C_6$ alkyl, which may be unsubstituted or substituted by one or more OH, (b) if $X^{C11}$ is not an aromatic carbocyclic group, Ph, $X^{C14}$-Ph, with Ph=phenyl, and (c) a $C_2$ to $C_4$ polyoxyalkylene group;

with the proviso that if $X^{C11}$ is a divalent 5 or 6 membered aromatic N-heterocyclic group, then $R^{C13}$ is unsubstituted or substituted by one OH with the exception that if $X^{C11}$ is a divalent 5 or 6 membered aromatic N-heterocyclic group comprising a first N atoms and a second heteroatom selected from N, then $R^{C13}$ is unsubstituted;

$R^{C14}$ is selected from H and a linear, branched or cyclic $C_1$-$C_6$ alkyl, preferably from H and a linear or branched $C_1$-$C_4$ alkyl, most preferably from H, methyl, ethyl, 1-propyl or 2-propyl;

n is 0 or an integer from 1 to 5, preferably 0, 1 or 2, most preferably 0 or 1.

Essentially, such complexing agents comprise a carbocyclic or heterocyclic moiety $X^{C11}$ to which one or two sulfur containing groups $R^{C11}$ are attached.

As used herein, "chemical bond" means that the respective moiety is not present but that the adjacent moieties are bridged so as to form a direct chemical bond between these adjacent moieties. By way of example, if in X-Y-Z the moiety Y is a chemical bond then the adjacent moieties X and Z together form a group X-Z.

Carbocyclic or Heterocyclic Group $X^{C11}$

In a first embodiment the divalent cyclic moiety $X^{C11}$ may be a 5 or 6 membered aromatic N-heterocyclic group which may be unsubstituted or substituted by one or more OH or one or more $R^{C14}$, particularly methyl, ethyl or propyl.

As used herein "5 or 6 membered" means that the cycle itself comprises 5 or 6 carbon atoms or heteroatoms, whereas substituents are not included.

In a first alternative of the first embodiment this heterocyclic aromatic moiety $X^{C11}$ may have a single N atom. An example of 5 membered N-heterocyclic group is, without limitation, pyrrole. An example of a 6 membered N-heterocyclic group is, without limitation, pyridine. All of these may be unsubstituted or substituted by one or more OH or one or more $R^{C14}$, particularly methyl, ethyl or propyl.

In a second alternative of the first embodiment this cyclic moiety $X^{C11}$ may have a first N atom and a second heteroatom selected from N and S, wherein the first N atom and the second heteroatom are separated by at least one C atom. Examples of 5 membered N-heterocyclic groups are, without limitation, imidazole, thiazole, or isothiazol. Examples of 6 membered N-heterocyclic groups are, without limitation, pyrimidine or pyrazine. All of these may be unsubstituted or substituted by one or more OH or one or more $R^{C14}$, particularly methyl, ethyl or propyl.

In a third alternative of the first embodiment this heterocyclic aromatic moiety $X^{C11}$ may be a triazole or a thiadiazole. All of these may be unsubstituted or substituted by one or more OH or one or more $R^{C14}$, particularly methyl, ethyl or propyl.

In a second embodiment cyclic moiety $X^{C11}$ may be a divalent 6 membered aromatic carbocyclic group which may be unsubstituted or substituted by one or more OH or one or more $R^{C14}$, particularly methyl, ethyl or propyl. Such aromatic carbocyclic group may be, but are not limited to, benzene, toluene, xylene, and hydroxybenzene.

In a third embodiment cyclic moiety $X^{C11}$ may be a divalent 5 or 6 membered aliphatic N-heterocyclic group comprising a first N atom and optionally a second heteroatom selected from N and O, which may be unsubstituted or substituted by one or more OH or one or more $R^{C14}$, particularly methyl, ethyl or propyl.

In a first alternative such divalent 5 or 6 membered aliphatic N-heterocyclic group may have only one N atom incorporated in the ring system, such as but not limited to pyrrolidine or piperidine, which are preferably substituted with $R^{C11}$ in the N-position.

In a second alternative such divalent 5 or 6 membered aliphatic N-heterocyclic group may have two N atoms incorporated in the ring system, such as but not limited to imidazolidine and piperazine, which may be unsubstituted or substituted by one or more OH or one or more $R^{C14}$, particularly methyl, ethyl or propyl.

In a third alternative such divalent 5 or 6 membered aliphatic N-heterocyclic group may have one N atom incorporated in the ring system and one O atom incorporated in the ring system or attached to the ring system. If the O atom is incorporated in the ring system it forms an ether group, if it is attached to it, it may be a C=O group. Examples of 5 membered heterocyclic group are, without limitation, N-pyrrolidone, N-oxazolidine, succinimide, and N-hydroxy succinimide. Preferred is N-pyrrolidone. An example of a 6 membered heterocyclic group is, without limitation, N-morpholine. All of these may be unsubstituted or substituted by one or more OH or one or more $R^{C14}$, particularly methyl, ethyl or propyl.

Sulfur-Containing Group $R^{C11}$

In a first embodiment the monovalent sulfur-containing group $R^{C\ 11}$ is selected from formula $-X^{C12}—S—[X^{C13}-D^{C11}]_n-R^{C13}$.

Herein the first divalent spacer group $X^{C12}$ may be a chemical bond or a linear, branched or cyclic $C_1$-$C_6$ alkanediyl, preferably a chemical bond or a linear or branched $C_1$ to $C_4$ alkanediyl, most preferably a chemical bond, methanediyl, ethanediyl or propanediyl. Such alkyl may be unsubstituted or substituted by OH. The inventors found that the complexing agents are only performing well under the condition that if $X^{C11}$ is a divalent 5 or 6 membered aromatic N-heterocyclic group, $R_{C13}$ is substituted by one OH and $R_{C12}$ is not $R^{C11}$, then $X_{C12}$ has to be a chemical bond.

If n>0 a further divalent spacer group $X^{C13}$ may be present. It may be a linear or branched $C_1$-$C_6$ alkanediyl, preferably a $C_1$ to $C_4$ alkyl, most preferably methanediyl, ethanediyl or propanediyl. Such alkyl may be unsubstituted or substituted by OH.

If n>0 further heteroatoms $D_{C11}$ may be present. Such heteroatoms $D^1$ may be one or more further sulfur atoms or one or more oxygen atoms.

In a first alternative $R^{C13}$ may be a linear, branched or cyclic $C_1$-$C_6$ alkyl, which may be unsubstituted or substituted by one or more OH. Preferably $R^{C13}$ may be a linear or branched $C_1$-$C_4$ alkyl, which may be unsubstituted or substituted by one or more OH. Most preferably $R^{C13}$ may be selected from methyl, ethyl, 1-propyl, 2-propyl, 2-hydroxyethyl, and 2,3-dihydroxypropyl.

However, in case $X^{C11}$ is a divalent 5 or 6 membered aromatic N-heterocyclic group, the complexing agents do only properly work if $R^{C13}$ is unsubstituted or substituted by only one OH with the exception that if $X^{C11}$ is a divalent 5 or 6 membered aromatic N-heterocyclic group comprising a first N atoms and a second heteroatom selected from N (i.e. the N-heterocyclic group comprises two N atoms), then $R^{C13}$ is unsubstituted.

In yet another alternative, under the condition that $X^{C11}$ is not an aromatic carbocyclic group, $R^{C13}$ may be Ph or $X^{C14}$-Ph. As used herein, Ph is phenyl. If the condition is not fulfilled, the complexing agents do not fulfill the required performance. In this embodiment, preferred groups $R^{C13}$ are Ph, hydroxyphenyl, benzyl, 2-phenylethyl, 2- or 3-phenylpropyl, and derivative thereof received by methylation or ethylation.

In yet another alternative $R^{C13}$ may be a $C_2$ to $C_4$ polyoxyalkylene group. Preferably $R^{C11}$ is a monovalent group of formula $-(O-CH_2-CHR^{C15})_m-OH$, wherein m may be an integer of from 2 to 20, preferably 2 to 10, most preferably 2 to 6. Since $R^{C13}$ may be prepared by polyalkoxylation of one or more alkylene oxides in this alternative it is also referred to herein as “polyalkylene oxide” or “polyoxyalkylene” group. $R^{C15}$ may be H, methyl or ethyl, preferably H or methyl, more preferably H or H and methyl. Most preferred polyoxyalkylene groups are polyoxyethylene or poly(oxyethylene-co-oxypropylene) groups. Polyoxyethylene groups are particularly preferred.

If n is 0, the sulfur-containing group $R^{C11}$ comprises only one sulfur atom. If n is 1 or more, a number of n further heteroatoms $D^1$ are present. Preferably n is 0 or an integer from 1 to 4, more preferably 0 or an integer from 1 to 3, even more preferably 0, 1 or 2, most preferably 0 or 1.

In another alternative $R^{C13}$ may be selected from H.

In a second embodiment the sulfur-containing group $R^{C11}$ is selected from

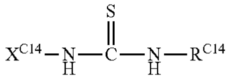

Herein, $R^{C14}$ may be selected from H and a linear or branched $C_1$-$C_6$ alkyl, preferably from H and a linear or branched $C_1$-$C_4$ alkyl, more preferably from H, methyl, ethyl or propyl, most preferably H.

$X^{C14}$ may be a chemical bond or a linear or branched $C_1$-$C_4$ alkanediyl, preferably a chemical bond, or methanediyl, ethanediyl, 1,2- or 1,3-propanediyl, most preferably a chemical bond.

In a third embodiment the sulfur-containing group $R^{C11}$ is selected from

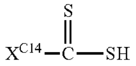

Herein, $X^{C14}$ may be a chemical bond or a linear or branched $C_1$-$C_4$ alkanediyl, preferably a chemical bond, or methanediyl, ethanediyl or propanediyl, most preferably a chemical bond.

Second Group $R^{C12}$

Besides a sulfur-containing group $R^{C11}$ a further monovalent group $R^{C12}$ is present in the complexing agent.

In a first alternative $R^{C12}$ is $R^{C11}$, i.e. a second sulfur containing group is present, which may be individually selected from groups $R^{C11}$. The first sulfur containing group and the second sulfur containing group may be the same or different, preferably the same. In this alternative the first sulfur containing group and the second sulfur containing group are directly linked to the same moiety $X^{C11}$.

In a second alternative $R^{C15}$ is selected from $X^{C11}$-$R^{C11}$, i.e. a second sulfur containing group is present, which may be individually selected from groups $R^{C11}$, like in alternative 1, but a second divalent heterocyclic group is present between the first divalent heterocyclic group $X^{C11}$ and the second sulfur containing group. The second divalent heterocyclic group and the first sulfur containing group may be the same or different, preferably the same. Typical nonlimiting example for such compounds comprising a first divalent heterocyclic group $X^{C11}$ and a second sulfur containing group are bibypridyl or biphenyl compounds.

In a third alternative $R^{C12}$ is selected from sulfur-free atoms/groups H, OH, $NR^{C14}{}_2$, linear, branched or cyclic $C_1$ to $C_{10}$ alkyl, and linear, branched or cyclic $C_1$ to $C_{10}$ alkoxy groups; These groups may be used to tune the specific properties like solubility in aqueous solutions, surface interactions, and the like to a desired level. In this embodiment preferred groups $R^{C12}$ are H, OH, $NH_2$, $NH(CH_3)$, $N(CH_3)_2$, $NH(C_2H_5)$, $N(C_2H_5)_2$, linear, branched or cyclic $C_1$ to $C_6$ alkyl, and linear branched or cyclic $C_1$ to $C_6$ alkoxy. More preferred groups $R^{C12}$ are H, OH, $NH_2$, linear or branched $C_1$ to $C_4$ alkyl, and liear or branched $C_1$ to $C_4$ alkoxy. Most preferred are H, OH, $NH_2$, methyl, ethyl, 1-propyl, 2-propyl, methoxy, ethoxy, and 1- or 2-propoxy.

Particularly preferred groups $R^{C12}$ are selected from $R^{C11}$, $X^{C11}$-$R^{C11}$, H, OH, and $NH_2$.

Particularly preferred embodiments of the complexing agents with $R^{C11}$ being selected from $-X^{C12}-S-[X^{C13}-D^{C11}]_n-R^{C13}$ are indicated in tables 1 to 3.

TABLE 1

Complexing agents with heterocyclic aromatic moieties $X^{C11}$

| $X^{C11*}$ | $R^{C12}$ | $D^{C11}$ | $X^{C12}$ | $X^{C13}$ | $R^{C13}$ | n |
|---|---|---|---|---|---|---|
| 2-Py | H | S | Et | Et | Et | 1 |
| 2,6-Py | $R^{C11}$ | S | Me | Et | Et | 1 |
| 2-Py | H | S | Me | Et | Et | 1 |
| 2-Py | H | n/a | bond | n/a | Et—OH | 0 |
| 2-Pyrimidine | H | n/a | bond | n/a | Et—OH | 0 |
| 2-Py | H | S | Et | Et | Et | 1 |
| 2-Py | H | S | Et | Et | Me | 1 |
| 2,6-Py | $X^{C11}$-$R^{C11}$ | S | Me | Et | Et | 1 |
| 2,6-Py | $R^{C11}$ | S | Me | Et | Me | 1 |
| N-Imidazole | H | S | Et | Et | Et | 1 |
| 2-Py | H | S | Et | Et | i-Pr | 1 |
| 2-Py | H | S | Me | Et | Me | 1 |
| 2-Py | H | S | Me | Et | Pr | 1 |
| 2-Thiazole | H | S | i-Pr | Et | Et | 1 |
| 2-Py | H | S | Et | Et | Bz | 1 |
| 2-Py | H | S | Et | Et | Ph | 1 |
| 1,2-Imidazole | Me | S | Me | Et | Et | 1 |
| 2,6-Py | $R^{C11}$ | S | Me | Et | Pr | 1 |
| 2,6-Pyrimidine | $R^{C11}$ | S | bond | Et | Pr | 1 |
| 2,6-Pyrimidine | $R^{C11}$ | S | bond | Et | Et | 1 |
| 2-Pyrazine | H | S | Et | Et | Et | 1 |
| 1,2-Imidazole | $Pr(OH)_2$ | n/a | bond | n/a | $Pr(OH)_2$ | 0 |
| 2,6-Py | $R^{C11}$ | n/a | bond | n/a | $Pr(OH)_2$ | 0 |
| 2,6-Py | $X^{C11}$-$R^{C11}$ | n/a | Me | n/a | $Pr(OH)_2$ | 0 |
| 3,5-Py | $R^{C11}$ | n/a | Me | n/a | $Pr(OH)_2$ | 0 |
| 2-Py | H | n/a | bond | n/a | EtOH | 0 |
| 1,2-Imidazole | Me | n/a | bond | n/a | EtOH | 0 |
| 2-Pyrimidine | H | n/a | bond | n/a | EtOH | 0 |
| 2-Thiazole | H | n/a | bond | n/a | EtOH | 0 |
| 2-Py | H | NH | bond | Et | EtOH | 1 |
| 2,5-Thiadiazole | $R^{C11}$ | n/a | bond | n/a | EtOH | 0 |
| 2,6-Py | $R^{C11}$ | n/a | Me | n/a | $Pr(OEt)_5$—OH | 1 |

TABLE 2

Complexing agents with carbocyclic aromatic moieties $X^{C11}$

| $X^{C11*}$ | $R^{C12}$ | $D^{C11}$ | $X^{C12}$ | $X^{C13}$ | $R^{C13}$ | n |
|---|---|---|---|---|---|---|
| 1,2 Ph | $R^{C11}$ | n/a | bond | n/a | $Pr(OH)_2$ | 0 |
| 3,4-Toluene | $R^{C11}$ | n/a | bond | n/a | $Pr(OH)_2$ | 0 |
| 1,4-Ph | $R^{C11}$ | n/a | Me | n/a | $Pr(OH)_2$ | 0 |
| 1,2 Ph | $R^{C11}$ | n/a | Me | n/a | $Pr(OH)_2$ | 0 |
| 1,2 Ph | $R^{C11}$ | n/a | bond | n/a | Et—OH | 0 |
| Ph | H | n/a | bond | n/a | Et—OH | 0 |
| Ph | OH | n/a | bond | n/a | Me | 0 |
| 1,3-Ph | $R^{C11}$ | n/a | Me | n/a | $Pr(OH)_2$ | 0 |

TABLE 2-continued

Complexing agents with carbocyclic aromatic moieties $X^{C11}$

| $X^{C11*}$ | $R^{C12}$ | $D^{C11}$ | $X^{C12}$ | $X^{C13}$ | $R^{C13}$ | n |
|---|---|---|---|---|---|---|
| 1,4-Ph | $R^{C11}$ | S | Me | Et | Et | 1 |
| 1,2-Ph | $R^{C11}$ | S | Me | Et | Et | 1 |
| 1,3-Ph | $R^{C11}$ | S | Me | Et | Et | 1 |
| 1,3-Ph | $R^{C11}$ | S | Me | Me | Me | 1 |
| Ph | H | n/a | bond | n/a | $Pr(OH)_2$ | 0 |
| $Me_2$—Ph | $R^{C11}$ | n/a | Me | n/a | $Pr(OH)_2$ | 0 |
| Ph | H | n/a | bond | n/a | EtOH | 0 |
| Ph | H | n/a | bond | n/a | EtOH | 0 |
| 1,3-Ph | $R^{C11}$ | n/a | Me | n/a | $Pr(OEt)_5$—OH | 1 |
| 1,4-Ph | $R^{C11}$ | n/a | bond | n/a | $Pr(OH)_2$ | 0 |
| 1,4-Ph | $R^{C11}$ | n/a | Et | n/a | $Pr(OH)_2$ | 0 |
| 1,2-Ph | $R^{C11}$ | n/a | bond | n/a | EtOH | 0 |
| 1,3-Ph | $R^{C11}$ | n/a | bond | n/a | $Pr(OH)_2$ | 0 |

TABLE 3

Complexing agents with heterocyclic aliphatic moieties $X^{C11}$

| $X^{C11*}$ | $R^{C12}$ | $D^{C11}$ | $X^{C12}$ | $X^{C13}$ | $R^{C13}$ | n |
|---|---|---|---|---|---|---|
| N-Morpholine | H | S | Et | Et | Et | 1 |
| N-Morpholine | H | S | Pr | Et | Et | 1 |
| N-Morpholine | H | S | Et | Et | Et | 1 |
| N-Morpholine | H | S | Me | Me | Me | 1 |
| N-Morpholine | H | S | Me | Et | Et | 1 |
| N-Morpholine | H | S | Et | Me | Me | 1 |
| N-Morpholine | H | n/a | Et | n/a | Et | 0 |
| N-Morpholine | H | n/a | Pr | n/a | Et | 0 |
| N-Morpholine | H | n/a | Me | n/a | Me | 0 |
| N-Morpholine | H | n/a | Pr | n/a | Me | 0 |
| N-Pyrrolidinone | H | S | Et | Et | Et | 1 |
| N-Pyrrolidinone | H | S | Me | Me | Me | 1 |
| N-Pyrrolidinone | H | S | Me | Me | Pr | 1 |
| N-Pyrrolidinone | H | n/a | Et | n/a | Et | 0 |
| N-Pyrrolidinone | H | n/a | Et | n/a | Me | 0 |
| N-Pyrrolidinone | H | n/a | Me | n/a | Pr | 0 |
| N-Pyrrolidinone | H | S | Et | Et | Pr | 1 |
| N-Pyrrolidinone | H | S | Pr | Et | Et | 1 |
| N-Piperidine | H | S | Et | Et | Et | 1 |
| N-Piperidine | H | S | Me | Me | Me | 1 |
| N-Piperidine | H | S | Pr | Me | Me | 1 |
| N-Piperidine | H | S | Me | Me | Pr | 1 |
| N-Piperidine | H | n/a | Et | n/a | Et | 0 |
| N-Piperidine | H | n/a | Me | n/a | Me | 0 |
| N-Piperidine | H | n/a | Pr | n/a | Me | 0 |
| N-Piperidine | H | n/a | Me | n/a | Pr | 0 |

*The numbers indicate the position of substituents $R^{C11}$ and $R^{C12}$ in $X^{C11}$ (H substitution skipped)

Abbreviations in Tables 1, 2, and 3:
Me = methyl/methanediyl,
Et = ethyl/1,2-ethanediyl;
Pr = 1-propyl/1,3-propanediyl;
Et—OH = 2-hydroxyethyl;
$Pr(OH)_2$ = 2,3-dihydroxypropyl;
i-Pr = 2-propyl/1,2-propanediyl,
Ph = phenyl/phenylene,
OEt = oxyethylene.

Most preferred complexing agents are selected from: 3-[2-(2,3-dihydroxypropylsulfanyl)phenyl]sulfanylpropane-1,2-diol; 3-[2-(2,3-dihydroxypropylsulfanyl)-4-methyl-phenyl]sulfanylpropane-1,2-diol; 3-[[2-(2,3-dihydroxypropylsulfanylmethyl)phenyl]methylsulfanyl]propane-1,2-diol; 2,6-bis(2-ethylsulfanylethylsulfanylmethyl)pyridine; morpholine-4-carbodithioate tetramethylammonium salt; piperazine-1,4-dicarbodithioate ditetramethylammonium salt; 3-[[3-(2,3-dihydroxypropylsulfanylmethyl)phenyl]methylsulfanyl]propane-1,2-diol; 2-[2-(2-propylsulfanylethylsulfanyl)ethyl]pyridine; 2-[2-(2-methylsulfanylethylsulfanyl)ethyl]pyridine; 2-(2-ethylsulfanylethylsulfanylmethyl)-6-[6-(2-ethylsulfanylethylsulfanylmethyl)-2-pyridyl]pyridine; 2,6-bis(2-methylsulfanylethylsulfanylmethyl)pyridine; 4-[2-(2-ethylsulfanylethylsulfanyl)ethyl]morpholine; 2-[2-(2-isopropylsulfanylethylsulfanypethyl]pyridine; 2-(2-propylsulfanylethylsulfanylmethyl)pyridine; 2-[2-(2-ethylsulfanylethylsulfanyl)-1-methyl-ethyl]thiazole; 2-[2-(2-benzylsulfanylethylsulfanyl)ethyl]pyridine; and 2-[2-(2-phenylsulfanylethylsulfanyl)ethyl]pyridine; and their salts.

Other Complexing Agents

The tin silver alloy electroplating bath may further contain additional complexing agents for complexing tin and/or any other metal present in the composition. A typical other complexing agent is 3,6-Dithia-1,8-octanediol.

Other typical complexing agents are polyoxy monocarboxylic acids, polycarboxylic acids, aminocarboxylic acids, lactone compounds, and salts therof.

Other complexing agents are organic thiocompounds like thiourea, thiols or thioethers as disclosed in U.S. Pat. No. 7,628,903, JP 4296358 B2, EP 0854206 A and U.S. Pat. No. 8,980,077 B2.

It is preferred that the tin alloy bath comprises no other complexing agents except those according to the invention.

A large variety of other additives may typically be used in the bath to provide desired surface finishes for the plated tin alloy bump. Usually more than one additive is used with each additive forming a desired function. Advantageously, the electroplating baths may further contain one or more of suppressing agents (also often referred to as surfactants), grain refiners, antioxidants, and mixtures thereof. Other additives may also be suitably used in the present electroplating baths.

Suppressing Agents or Surfactants

One or more suppressing agents (also referred to as surfactants) may be present in the tin-silver alloy plating bath.

Any nonionic surfactant may be used in the present compositions. Typically, the nonionic surfactants have an average molecular weight from 200 to 100000, preferably from 500 to 50000, more preferably from 500 to 25000, and yet more preferably from 750 to 15000. Such nonionic surfactants are typically present in the electrolyte compositions in a concentration from 1 to 10000 ppm, based on the weight of the composition, and preferably from 5 to 10000 ppm. Preferred alkylene oxide compounds include polyalkylene glycols, such as but not limited to alkylene oxide addition products of an organic compound having at least one hydroxy group and 20 carbon atoms or less and tetrafunctional polyethers derived from the addition of different alkylene oxides to low molecular weight polyamine compounds.

Preferred polyalkylene glycols are polyethylene glycol and polypropylene glycol. Such polyalkylene glycols are generally commercially available from a variety of sources and may be used without further purification. Capped polyalkylene glycols where one or more of the terminal hydrogens are replaced with a hydrocarbyl group may also be suitably used. Examples of suitable polyalkylene glycols are those of the formula R—O—$(CXYCX'Y'O)_n$R' where R and R' are independently chosen from H, $C_2$-$C_{20}$ alkyl group and $C_6$-$C_{20}$ aryl group; each of X, Y, X' and Y' is independently selected from hydrogen, alkyl such as methyl, ethyl or propyl, aryl such as phenyl, or aralkyl such as benzyl; and n is an integer from 5 to 100,000. Typically, one or more of X, Y, X' and Y' is hydrogen.

Suitable EO/PO copolymers generally have a weight ratio of EO:PO of from 10:90 to 90:10, and preferably from 10:90 to 80:20. Such EO/PO copolymers preferably have an average molecular weight of from 750 to 15,000. Such EO/PO copolymers are available from a variety of sources, such as those available from BASF under the tradename "PLURONIC".

Suitable alkylene oxide condensation products of an organic compound having at least one hydroxy group and 20 carbon atoms or less include those having an aliphatic hydrocarbon from one to seven carbon atoms, an unsubstituted aromatic compound or an alkylated aromatic compound having six carbons or less in the alkyl moiety, such as those disclosed in U.S. Pat. No. 5,174,887. The aliphatic alcohols may be saturated or unsaturated. Suitable aromatic compounds are those having up to two aromatic rings. The aromatic alcohols have up to 20 carbon atoms prior to derivatization with ethylene oxide. Such aliphatic and aromatic alcohols may be further substituted, such as with sulfate or sulfonate groups.

Preferred surfactants are those of formula S1:

(S1)

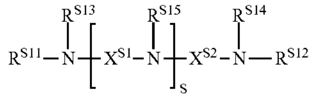

The compounds of formula S1 may be prepared by reacting a polyamine starter with one or more $C_2$ to $C_6$ alkylene oxides to form the respective amine-based suppressing agents.

Generally, s may be an integer of from 1 to 6. Preferably s is an integer from 1 to 4, most preferably s is 1 or 2.

$X^{S1}$ and $X^{S2}$ are a divalent spacer group within the polyamine starter. They may independently be selected from a linear or branched $C_1$-$C_{12}$ alkanediyl. Such alkanediyl spacer are unsubstituted but may optionally be interrupted by O or S. $X^{S1}$ and $X^{S2}$ may be the same or different, preferably the same. In a first preferred embodiment $X^{S1}$ and $X^{S2}$ are $C_1$-$C_6$ alkanediyl, more preferably $C_1$-$C_4$ alkanediyl, most preferably methanediyl, ethanediyl or propanediyl. In a second preferred embodiment heteroatoms are present and $X^{S1}$ and $X^{S2}$ may be —$(CHR^{41})_q$-[Q-$(CHR^{41})_r]_v$-, with Q being selected from O or S wherein q+r·v is the number of C atoms in the spacer. Particularly preferred is a spacer with Q=O and q=r=1 or 2.

$R^{S11}$ is a monovalent group of formula —(O—$CH_2$—$CHR^{S41})_m$—$OR^{S42}$, wherein m is an integer of from 2 to 250, preferably 3 to 120, most preferably 10 to 65. Since $R^{S11}$ may be prepared by polyalkoxylation of one or more alkylene oxides it is also referred to herein as "polyalkylene oxide" or "polyoxyalkylene". $R^{S41}$ is selected from H and a linear or branched $C_1$ to $C_5$ alkyl, preferably from H and a linear or branched $C_1$ to $C_3$ alkyl, more preferably from H, methyl, ethyl and n-propyl, most preferably from H or methyl. $R^{S42}$ is selected from H and a linear or branched $C_1$-$C_{20}$ alkyl, which may optionally be substituted by hydroxy, alkoxy or alkoxycarbonyl, preferably from H and a linear or branched $C_1$ to $C_{10}$ alkyl, more preferably from H and methyl, ethyl, propyl or butyl, most preferably H.

Generally, $R^{S12}$, $R^{S13}$, $R^{S14}$ are independently selected from H, $R^{S11}$ and $R^{S40}$, preferably from $R^{S11}$ and $R^{S40}$, most preferably from $R^{S11}$.

$R^{S40}$ is a linear or branched $C_1$-$C_{20}$ alkyl. Preferably $R^{S40}$ is $C_1$-$C_{10}$ alkyl, even more preferably $C_1$-$C_6$ alkyl, most preferably methyl, ethyl or propyl.

$R^{S42}$ is a linear or branched $C_1$-$C_{20}$ alkyl, which may optionally be substituted by hydroxy, alkoxy or alkoxycarbonyl. Preferably $R^{S42}$ is an unsubstituted linear or branched $C_1$-$C_{20}$ alkyl.

Generally, $R^{S15}$ is selected from H, $R^{S11}$, $R^{S40}$, and -$X^{S4}$—N $(R^{S21})_2$ with $R^{S21}$ being selected from $R^{S11}$ and $R^{S40}$, preferably from $R^{S11}$.

In a preferred embodiment $R^{S15}$ is selected from $R^{S11}$ and -$X^{S4}$—$N(R^{S11})_2$. In another preferred embodiment $R^{S15}$ is selected from $R^{S40}$ and -$X^{S4}$—$N(R^{S40})_2$.

In one embodiment $X^{S4}$ is a linear or branched $C_1$ to $C_{12}$ alkanediyl. Preferably $X^{S4}$ is a $C_1$ to $C_6$ alkanediyl, more preferably methanediyl, ethanediyl, propanediyl or butanediyl, most preferably methanediyl or ethanediyl.

In another embodiment $X^{S4}$ is a divalent group which is selected from a $C_2$ to $C_6$ polyoxyalkylene group of formula —(O—$CH_2$—$CHR^{S41})_o$— (hereinafter also referred to as polyalkylene oxide group). Herein o may be an integer from 1 to 250, preferably from 2 to 120, most preferably from 5 to 65. The $C_2$ to $C_6$ polyoxyalkylene group may be prepared from the one or more respective alkylene oxides. Preferably the at least one $C_2$ to $C_6$ polyoxyalkylene group is selected from polyoxyethylen (prepared from ethylene oxide), polyoxypropylene (prepared from propylene oxide), and polyoxybutylene (prepared from butylene oxide). More preferably the polyoxyalkylene group in $X^{S4}$ is a copolymer of ethylene oxide and at least one further $C_3$ to $C_6$ alkylene oxide. The further alkylene oxide is preferably selected from propylene oxide and 1,2-butylene oxide or any isomers thereof. In another preferred embodiment the $C_3$ to $C_4$ alkylene oxide is selected from propylene oxide (PO). In this case EO/PO copolymer side chains are generated from the starting molecule. Such copolymers of ethylene oxide and at least one further alkylene oxide may have random, block, alternating or any other arrangement.

As used herein, "random" means that the comonomers are polymerized from a mixture and therefore arranged in a statistically manner depending on their copoymerization parameters.

As used herein, "block" means that the comonomers are polymerized after each other to form blocks of the respective co-monomers in any predefined order. By way of example, for EO and propylene oxide (PO) comonomers such blocks may be, but are not limited to: -$EO_x$-$PO_y$, -$PO_x$-$EO_y$, -$EO_x$-$PO_y$-$EO_z$, -$PO_x$-$EO_y$-$PO_z$, etc. Preferred block-type alkylene oxides are -$PO_x$-$EO_y$, and -$EO_x$-$PO_y$-$EO_z$ wherein x is in the range of 2 to 300, y is in the range of 2 to 300, and z is in the range of 2 to 300.

In a preferred embodiment, block -$PO_x$-$EO_y$ or -$EO_x$-$PO_y$-$EO_z$ copolymers comprising a terminal ethylene oxide block are used, wherein the PO units may be exchanged by another $C_4$ to $C_6$ alkylene oxide.

If copolymers of ethylene oxide (EO) and a further $C_3$ to $C_4$ alkylene oxide are used the EO content may generally be from 3 to 95% by weight. Preferably the EO content is from 5 to 80% by weight, more preferably from 5 to 60% by weight, even more preferably below 50% by weight, even more preferably below 40% by weight, even more preferably from 5 to 40% by weight, even more preferably from 5 to 30% by weight, even more preferably from 6 to 25% by weight, most preferably from 8 to 20% by weight.

Generally, the molecular weight $M_w$ of the suppressing agent may be from about 500 to about 30000 g/mol, preferably 2000 to 15000 g/mol. In one embodiment the molecular weight $M_w$ of the suppressing agent is from about 500 to about 8000 g/mol, most preferably from about 1500 to about 3500 g/mol. In another embodiment the molecular weight $M_w$ of the suppressing agent is from about 5000 to about 20000 g/mol, in particular from about 6000 to about 15000 g/mol.

In a first preferred embodiment a compound of formula I is used in which s is 1, 2 or 3, most preferably 1 or 2; and $R^{S12}$, $R^{S13}$, $R^{S13}$ and $R^{S15}$ are independently selected from a $C_2$ to $C_6$ polyoxyalkylene group $R^{S11}$. Such compounds may be prepared by starting from symmetric dialkylentriamines, trialkylenetetramines, tetraalkylenpentamins, such as but not limited to diethylentriamine, triethylenetetramine, dipropylentriamine, tripropylentetramine, methyl diethylentriamine, dimethyl triethylenetetramine, and the like.

In a second preferred embodiment a compound of formula I is used in which s is 1, 2 or 3, most preferably 1 or 2; $R^{S12}$, $R^{S13}$, $R^{S14}$ are independently selected from a $C_2$ to $C_6$ polyoxyalkylene group $R^{S11}$; and $R^{S15}$ is selected from $X^{S4}$-N $(R^{S11})_2$. In this way, a more branched polyoxyalkylene suppressing agent is received. Such compounds may be prepared by starting from branched amine starters, such as but not limited to tris aminoethyl amine and the like.

In a third preferred embodiment n is 1, 2 or 3, most preferably 1 or 2; $R^{S12}$, $R^{S13}$ and $R^{S14}$ are selected from a $C_2$ to $C_6$ polyoxyalkylene group $R^{S11}$, and $R^{S15}$ is selected from $R^{S40}$, and -$X^{S4}$—N$(R^{S40})_2$. In this way, a linear or branched suppressing agent is received which comprises, besides the polyoxyalkylene side chains, also one or more alkyl-substituents. Such compounds may be prepared by starting from linear amines as described above, wherein the secondary amino group(s) are alkyl substituted, or starting from branched amines in which one or more amine groups are alkyl substituted, such as but not limited to tris alkylaminoethyl amine and the like.

In a fourth preferred embodiment s is 1, 2 or 3, preferably 1 or 2, most preferably 1; $R^{S12}$ is selected from $R^{S11}$; $R^{S13}$ and $R^{S14}$ are selected from $R^{S40}$, and $R^{S15}$ is selected from $R^{S21}$. Such compounds may be prepared by starting from symmetrically alkyl substituted dialkylentriamines or trialkylenetetramines, such as but not limited to N,N-dimethyl diethylenetriamine, N,N,N-trimethyl diethylenetriamine, and the like.

In a fifth preferred embodiment n is 1, 2 or 3, preferably 1 or 2, most preferably 1; and $R^{S13}$ is selected from $R^{S11}$; and at least one of $R^{S12}$ and $R^{S14}$ is selected from $R^{S40}$; and $R^{S15}$ is selected from $R^{S21}$. Such compounds may be prepared by starting from asymmetric dialkylentriamines or trialkylenetetramines, such as but not limited to 1-N-methyl diethylenetriamine, 1,3-N-dimethyl diethylenetriamine, and the like.

Particularly preferred embodiments suppressing agents of formula I are those wherein (a) $X^{S1}$ and $X^{S2}$ are ethanediyl or propanediyl, $R^{S11}$, $R^{S12}$, $R^{S13}$, $R^{S14}$, and $R^{S15}$ are a polyoxyalkylene, particularly an oxyethylene-co-oxypropylene polymer, (b) $X^{S1}$ and $X^{S2}$ are ethanediyl or propanediyl, $R^{S11}$, $R^{S12}$, $R^{S13}$, and $R^{S14}$ are a polyoxyalkylene, particularly a oxyethylene-co-oxypropylene polymer, and $R^{S15}$ is $C_1$ to $C_6$ alkyl or a polyoxyalkylene substituted $C_1$ to $C_6$ alkyl, and (c) $X^{S1}$ and $X^{S2}$ are ethanediyl or propanediyl, $R^{S11}$, $R^{S12}$, $R^{S13}$, and $R^{S14}$ are a polyoxyalkylene, particularly an oxyethylene-co-oxypropylene polymer, and $R^{S15}$ is a $C_1$ to $C_6$ amine which is further substituted by a polyoxyalkylene, particularly oxyethylene-co-oxypropylene polymers.

Levelers

One or more levelers may be present in the tin or tin alloy plating bath.

On class of levelers are linear or branched polyimidazolium compounds comprising the structural unit of formula L1

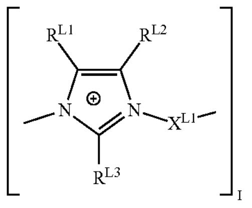

Generally, $R^{L1}$ and $R^{L2}$ may be an H atom or an organic radical having from 1 to 20 carbon atoms. The radicals can be branched or unbranched or comprise functional groups which can, for example, contribute to further crosslinking of the polymeric imidazolium compound. Preferably, $R^{L1}$ and $R^{L2}$ are each, independently of one another, hydrogen atoms or hydrocarbon radicals having from 1 to 6 carbon atoms. Most preferably $R^{L1}$ and $R^{L2}$ are H atoms.

Generally, $R^{L3}$ may be an H atom or an organic radical having from 1 to 20 carbon atoms.

Preferably, $R^{L3}$ is an H atom or methyl, ethyl or propyl. Most preferably $R^{L3}$ is an H atom.

Generally, $X^{L1}$ may be a linear, branched or cyclic aliphatic diradical selected from a $C_4$ to $C_{20}$ alkandiyl, which may comprise one or more continuations of the imidazolium compound by branching.

As used herein, "continuation of the polyimidazolium compound by branching" means that the respective spacer group $X^{L1}$ comprises one or more, preferably one or two, groups from which a polyimidazole branch is started. Preferably, $X^{L1}$ does not comprise any continuation of the polyimidazolium compound by branching, i.e. the polyimidazolium compound is a linear polymer.

In a first embodiment $X^{L1}$ is $C_4$ to $C_{14}$ alkanediyl, most preferably $C_4$ to $C_{12}$ alkanediyl, which may be unsubstituted or substituted by $OR^{L4}$, $NR^{L4}_2$, and $S^LR^4$, in which $R^{L4}$ is a $C_1$ to $C_4$ alkyl group. In a particular embodiment, $X^{L1}$ is a pure hydrocarbon radical which does not comprise any functional groups.

Particularly preferred groups $X_{L1}$ are selected from a linear or branched butanediyl, pentanediyl, hexanediyl, heptanediyl, octanediyl, nonanediyl, decanediyl, undecanediyl, and dodecanediyl, which may be unsubstituted or substituted by $OR^{L4}$, $NR^{L4}$. Particularly preferred groups $X^{L1}$ are selected from linear butanediyl, hexanediyl and octanediyl.

In second embodiment, group $X^{L1}$ may be a cyclic alkanediyl of formula

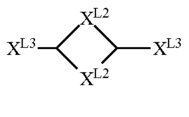

wherein $X^{L2}$ is independently selected from a $C_1$ to $C_4$ alkandiyl, which may be interrupted by one or two selected from O and $NR^{L4}$, and $X^{L3}$ is independently selected from (a) a chemical bond or (b) a $C_1$ to $C_4$ alkandiyl, which may be interrupted by O or $NR^{L4.}$ wherein $R^{L4}$ is a $C_1$ to $C_4$ alkyl group.

Either $X^{L2}$ or $X^{L3}$ or both $X^{L2}$ and $X^{L3}$ may comprise one or more continuations of the imidazolium compound by branching, preferably only $X^2$ may comprise such continuations of the imidazolium compound by branching.

In this second embodiment, most preferably one $X^{L2}$ is selected from methanediyl and the other $X^{L2}$ is selected from propanediyl or both $X^{L2}$ are selected from ethanediyl. Particularly preferred are groups $X^{L1}$ are selected from isophoronediamine, biscyclohexyldiamino methane, and methyl-cyclohexyl-diamine (MDACH).

In a third embodiment, $X^{L1}$ may be a (hetero)arylalkyl diradical selected from $Y^{L2}$-$Y^{L1}$-$Y^{L2}$. Herein $Y^{L1}$ may be a $C_5$ to $C_{20}$ aryl group and $Y^{L2}$ may be independently selected from a linear or branched $C_1$ to $C_6$ alkanediyl. Also here, both, $Y^{L1}$ and $Y^{L2}$ may comprise one or more continuations of the imidazolium compound by branching.

Preferred groups $Y^{L1}$ are selected from phenyl, naphtyl, pyridyl, pyrimidyl, and furanyl, most preferably phenyl. Preferred groups $Y^{L2}$ are selected from a linear or branched $C_1$ to $C_4$ alkanediyl, preferably from methanediyl, ethanediyl, 1,3-propanediyl and 1,4-butanediyl.

The organic radical $X^{L1}$ may comprise not only carbon and hydrogen but also heteroatoms such as oxygen, nitrogen, sulfur or halogens, e.g. in the form of functional groups such as hydroxyl groups, ether groups, amide groups, aromatic heterocycles, primary, secondary, or tertiary amino groups or imino groups.

In particular, the organic radical $X^{L1}$ may be a hydrocarbon diradical which may be substituted or interrupted by functional groups comprising heteroatoms, in particular ether groups. If substituted, it is preferred that $X^{L1}$ does not comprise any hydroxyl groups.

I may generally be an integer from 2 to about 5000, preferably from about 5 to about 3000, even more preferably from about 8 to about 1000, even more preferably from about 10 to about 300, even more preferably from about 15 to about 250, most preferably from about 25 to about 150.

The mass average molecular weight M w of the additive may generally be from 500 g/mol to 1,000,000 g/mol, preferably from 1000 g/mol to 500,000 g/mol, more preferably from 1500 g/mol to 100,000 g/mol, even more preferably from 2,000 g/mol to 50,000 g/mol, even more preferably from 3,000 g/mol to 40,000 g/mol, most preferably from 5,000 g/mol to 25,000 g/mol.

Preferably the at least one additive comprises a counterion $Y^{o-}$, wherein o is a positive integer selected so that the overall additive is electrically neutral. Preferably o is 1, 2 or 3. Most preferably, the counterion $Y^{o-}$ is selected from chloride, sulfate, methanesulfonate or acetate.

Preferably the number average molecular weight $M_n$ of the polymeric imidazolium compound, determined by gel permeation chromatography, is be greater than 500 g/mol.

Preferably the polymeric imidazolium compound may comprise more than 80% by weight of structural units of the formula L1.

More details and alternatives are described in unpublished European patent application No. 17173987.3, patent publication WO 2016/020216 and International Patent Application No. PCT/EP2017/050054, respectively, which are incorporated herein by reference.

Other suitable leveling agents include, but are not limited to, polyaminoamide and derivatives thereof, polyalkanolamine and derivatives thereof, polyethylene imine and derivatives thereof, quaternized polyethylene imine, polyglycine, poly(allylamine), polyaniline, polyurea, polyacrylamide, poly(melamine-co-formaldehyde), reaction products of amines with epichlorohydrin, reaction products of an amine, epichlorohydrin, and polyalkylene oxide, reaction products of an amine with a polyepoxide, polyvinylpyridine, polyvinylimidazole, polyvinylpyrrolidone, or copolymers thereof, nigrosines, pentamethyl-para-rosaniline hydrohalide, hexamethyl-pararosaniline hydrohalide, or compounds containing a functional group of the formula N-R-S, where R is a substituted alkyl, unsubstituted alkyl, substituted aryl or unsubstituted aryl. Typically, the alkyl groups are $C_1$-$C_6$ alkyl and preferably $C_1$-$C_4$ alkyl. In general, the aryl groups include $C_6$-$C_{20}$ aryl, preferably $C_6$-$C_{12}$ aryl. Such aryl groups may further include heteroatoms, such as sulfur, nitrogen and oxygen. It is preferred that the aryl group is phenyl or napthyl. The compounds containing a functional group of the formula N-R-S are generally known, are generally commercially available and may be used without further purification.

In such compounds containing the N-R-S functional group, the sulfur ("S") and/or the nitrogen ("N") may be attached to such compounds with single or double bonds. When the sulfur is attached to such compounds with a single bond, the sulfur will have another substituent group, such as but not limited to hydrogen, $C_1$-$C_{12}$ alkyl, $C_2$-$C_{12}$ alkenyl, $C_6$-$C_{20}$ aryl, $C_1$-$C_{12}$ alkylthio, $C_2$-$C_{12}$ alkenylthio, $C_6$-$C_{20}$ arylthio and the like. Likewise, the nitrogen will have one or more substituent groups, such as but not limited to hydrogen, $C_1$-$C_{12}$ alkyl, $C_2$-$C_{12}$ alkenyl, $C_7$-$C_{10}$ aryl, and the like. The N-R-S functional group may be acyclic or cyclic. Compounds containing cyclic N-R-S functional groups include those having either the nitrogen or the sulfur or both the nitrogen and the sulfur within the ring system.

Further leveling agents are triethanolamine condensates as described in unpublished international Patent Application No. PCT/EP2009/066581.

In general, the total amount of leveling agents in the electroplating bath is from 0.5 ppm to 10000 ppm based on the total weight of the plating bath. The leveling agents according to the present invention are typically used in a total amount of from about 100 ppm to about 10000 ppm based on the total weight of the plating bath, although greater or lesser amounts may be used.

Grain Refiners

The tin or tin alloy electroplating bath may further contain grain refiners. Grain refiners may be chosen from a compound of formula G1 or G2

(G1)

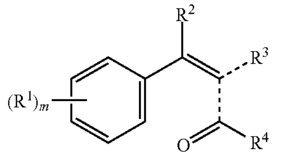

-continued (G2)

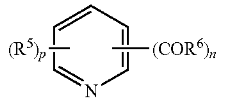

wherein each $R^1$ is independently $C_1$ to $C_6$ alkyl, $C_1$ to $C_6$ alkoxy, hydroxy, or halogen; $R_2$ and $R_3$ are independently selected from H and $C_1$ to $C_6$ alkyl; $R^4$ is H, OH, $C_1$ to $C_6$ alkyl or $C_1$ to $C_6$ alkoxy; m is an integer from 0 to 2; each $R^5$ is independently $C_1$ to $C_6$ alkyl; each $R^6$ is independently chosen from H, OH, $C_1$ to $C_6$ alkyl, or $C_1$ $C_6$ alkoxy; n is 1 or 2; and p is 0, 1 or 2.

Preferably, each $R^1$ is independently $C_1$ to $C_6$ alkyl, $C_1$ to $C_3$ alkoxy, or hydroxy, and more preferably $C_1$ to $C_4$ alkyl, $C_1$ to $C_2$ alkoxy, or hydroxy. It is preferred that $R^2$ and $R^3$ are independently chosen from H and $C_1$ to $C_3$ alkyl, and more preferably H and methyl. Preferably, $R^4$ is H, OH, $C^1$ to $C^4$ alkyl or $C_1$ to $C_4$ alkoxy, and more preferably H, OH, or $C_1$ to $C_4$ alkyl. It is preferred that $R^5$ is $C_1$ to $C_4$ alkyl, and more preferably $C_1$ to $C_3$ alkyl. Each $R^6$ is preferably chosen from H, OH, or C1 to $C_6$ alkyl, more preferably H, OH, or $C_1$ to $C_3$ alkyl, and yet more preferably H or OH. It is preferred that m is 0 or 1, and more preferably m is 0. Preferably, n is 1. It is preferred that p is 0 or 1, and more preferably p is 0. A mixture of first grain refiners may be used, such as two different grain refiners of formula 1, 2 different grain refiners of formula 2, or a mixture of a grain refiner of formula 1 and a grain refiner of formula 2.

Exemplary compounds useful as such grain refiners include, but are not limited to, cinnamic acid, cinnamaldehyde, benzalacetone, picolinic acid, pyridinedicarboxylic acid, pyridinecarboxaldehyde, pyridinedicarboxaldehyde, or mixtures thereof. Preferred grain refiners include benzalacetone, 4-methoxy benzaldehyde, benzylpyridin-3-carboxylate, and 1,10-phenantroline.

Further grain refiners may be chosen from an α,β-unsaturated aliphatic carbonyl compound. Suitable α,β-unsaturated aliphatic carbonyl compound include, but are not limited to, α,β-unsaturated carboxylic acids, α,β-unsaturated carboxylic acid esters, α,β-unsaturated amides, and α,β-unsaturated aldehydes. Preferably, such grain refiners are chosen from α,β-unsaturated carboxylic acids, α,β-unsaturated carboxylic acid esters, and α,β-unsaturated aldehydes, and more preferably α,β-unsaturated carboxylic acids, and α,β-unsaturated aldehydes. Exemplary α,β-unsaturated aliphatic carbonyl compounds include (meth) acrylic acid, crotonic acid, C to C6 alkyl meth)acrylate, (meth)acrylamide, $C_1$ to $C_6$ alkyl crotonate, crotonamide, crotonaldehyde,(meth)acrolein, or mixtures thereof. Preferred α,β-unsaturated aliphatic carbonyl compounds are (meth)acrylic acid, crotonic acid, crotonaldehyde, (meth) acrylaldehyde or mixtures thereof.

In one embodiment, grain refiners may be present in the plating baths in an amount of 0.0001 to 0.045 g/l. Preferably, the grain refiners are present in an amount of 0.0001 to 0.04 g/l, more preferably in an amount of 0.0001 to 0.035 g/l, and yet more preferably from 0.0001 to 0.03 g/l. Compounds useful as the first grain refiners are generally commercially available from a variety of sources and may be used as is or may be further purified.

In another more preferred embodiment, the compositions for tin or tin alloy electroplating do comprises a single grain refiner, more preferably a single grain refiner that is no α,β-unsaturated aliphatic carbonyl compound, most preferably essentially no grain refiner or no grain refiner at all. Surprisingly, it was found that particularly for filling recessed features having an aperture size below 50 μm there is no need to use any grain refiners but the suppressing agent leads to a good coplanarity without the use of any grain refiner.

The present compositions may optionally include further additives, such as antioxidants, organic solvents, complexing agents, and mixtures thereof.

Antioxidants

Antioxidants may optionally be added to the present composition to assist in keeping the tin in a soluble, divalent state. It is preferred that one or more antioxidants are used in the present compositions. Exemplary antioxidants include, but are not limited to, hydroquinone, and hydroxylated and/or alkoxylated aromatic compounds, including sulfonic acid derivatives of such aromatic compounds, and preferably are: hydroquinone; methylhydroquinone; resorcinol; catechol; 1,2,3-trihydroxybenzene; 1,2-dihydroxybenzene-4-sulfonic acid; 1,2-dihydroxybenzene-3,5-disulfonic acid; 1,4-dihydroxybenzene-2-sulfonic acid; 1,4-dihydroxybenzene-2,5-disulfonic acid; 2,4-dihyroxybenzene sulfonic acid, and p-Methoxyphenol. Such antioxidants are disclosed in U.S. Pat. No. 4,871,429. Other suitable antioxidants or reducing agents include, but are not limited to, vanadium compounds, such as vanadylacetylacetonate, vanadium triacetylacetonate, vanadium halides, vanadium oxyhalides, vanadium alkoxides and vanadyl alkoxides. The concentration of such reducing agent is well known to those skilled in the art, but is typically in the range of from 0.1 to 10 g/l, and preferably from 1 to 5 g/l. Such antioxidants are generally commercially available from a variety of sources.

Electrolyte

In general, as used herein "aqueous" means that the present electroplating compositions comprises a solvent comprising at least 50% of water. Preferably, "aqueous" means that the major part of the composition is water, more preferably 90% of the solvent is water, most preferably the solvent essentially consists of water. Any type of water may be used, such as distilled, deinonized or tap.

The bath comprises tin and silver ions. Preferably the bath comprises metal ions essentially consisting of tin ions and silver ions, i.e. there are essentially no metal ions present besides tin ions and silver ions. Essentially free of any other metal ions means that the metal ion concentration in the bath is below 1% by weight, preferably below 0.1% by weight, most preferably below 0.01% by weight.

Tin

The tin ion source may be any compound capable of releasing metal ions to be deposited in the electroplating bath in sufficient amount, i.e. is at least partially soluble in the electroplating bath. It is preferred that the metal ion source is soluble in the plating bath. Suitable metal ion sources are metal salts and include, but are not limited to, metal sulfates, metal halides, metal acetates, metal nitrates, metal fluoroborates, metal alkylsulfonates, metal arylsulfonates, metal sulfamates, metal gluconates and the like.

The metal ion source may be used in the present invention in any amount that provides sufficient metal ions for electroplating on a substrate. When the metal is solely tin, the tin salt is typically present in an amount in the range of from about 1 to about 300 g/l of plating solution. In a preferred embodiment the plating solution is free of lead, that is, they contain 1 wt % lead, more preferably below 0.5 wt %, and yet more preferably below 0.2 wt %, and still more preferably are free of lead. In another preferred embodiment the plating solution is essentially free of copper, that is, they contain below 1 wt % copper, more preferably below 0.1 wt %, and yet more preferably below 0.01 wt %, and still more preferably are free of copper.

Silver

Besides tin, the plating baths according to the invention contains silver ions and optionally one or more other alloying metal ions. Suitable alloying metals include, without limitation, gold, copper, bismuth, indium, zinc, antimony, manganese and mixtures thereof. Preferred alloying metals are copper, bismuth, indium, and mixtures thereof. Any bath-soluble salt of silver and other alloying metal (together referred to as alloying metal) may suitably be used as the source of alloying silver and other alloy metal ions. Examples of such alloying metal salts include, but are not limited to: metal oxides; metal halides; metal fluoroborate; metal sulfates; metal alkanesulfonates such as metal methanesulfonate, metal ethanesulfonate and metal propanesulfonate; metal arylsulfonates such as metal phenylsulfonate, metal toluenesulfonate, and metal phenolsulfonate; metal carboxylates such as metal gluconate and metal acetate; and the like. Preferred alloying metal salts are metal sulfates; metal alkanesulfonates; and metal arylsulfonates. When silver is added to the present compositions, a binary alloy deposit is achieved. When 2, 3 or more different alloying metals are added to the present compositions, tertiary, quaternary or higher order alloy deposits are achieved. The amount of such alloying metal used in the present compositions will depend upon the particular tin-alloy desired. The selection of such amounts of alloying metals is within the ability of those skilled in the art. It will be appreciated by those skilled in the art that when certain alloying metals besides silver are used, an additional complexing agent besides the complexing agents according to the invention may be required.

The present electroplating compositions are suitable for depositing a tin-silver-containing layer, Exemplary tin-alloy layers include, without limitation, tin-silver-copper, tin-silver-indium, tin-silver-bismuth, tin-silver-copper-antimony, tin-silver-copper-manganese, tin-silver-zinc-copper, and tin-silver-indium-bismuth. Preferably, the present electroplating compositions deposit pure tin-silver, tin-silver-copper, tin-indium, tin-silver-bismuth, tin-silver-indium, and tin-silver-indium-bismuth, and more preferably pure tin-silver.

Silver alloys deposited from the present electroplating bath contain an amount of tin ranging from 0.01 to 99.99 wt %, and an amount of one silver and optionally other alloying metals ranging from 99.99 to 0.01 wt %, based on the weight of the alloy, as measured by either atomic adsorption spectroscopy (AAS), X-ray fluorescence (XRF), inductively coupled plasma mass spectrometry (ICP-MS). Preferably, the tin-silver alloys deposited using the present invention contain from 90 to 99.99 wt % tin and 0.01 to 10 wt % of silver and any other alloying metal.

More preferably, the tin-silver alloy deposits contain from 95 to 99.9 wt % tin and 0.1 to 5 wt % of silver and any other alloying metal. Tin-silver alloy is the preferred tin-alloy deposit, and preferably contains from 90 to 99.9 wt % tin and from 10 to 0.1 wt % silver. More preferably, the tin-silver alloy deposits contain from 95 to 99.9 wt % tin and from 5 to 0.1 wt % silver. For many applications, the eutectic composition of an alloy may be used. Alloys deposited according to the present invention are substantially free of lead, that is, they contain 1 wt % lead, more preferably below 0.5 wt %, and yet more preferably below 0.2 wt %, and still more preferably are free of lead.

Bath

In general, besides the metal ion source and at least one of the complexing agents, the present metal electroplating compositions (also referred to as "electroplating bath") preferably include electrolyte, i.e. acidic or alkaline electrolyte, one or more sources of metal ions, optionally halide ions, and optionally other additives like surfactants and grain refiners. Such baths are typically aqueous, i.e. they do not comprise any further solvent(s) besides water. The water may be present in a wide range of amounts. Any type of water may be used, such as distilled, deionized or tap. Preferably the tin silver electroplating bath is a homogeneous solution, i.e. is essentially free of any particles. Essentially free of particles here means that such particles do not interfere with the metal electroplating process.

Preferably, the plating baths of the invention are acidic, that is, they have a pH below 7. Typically, the pH of the tin or tin alloy electroplating composition is below 4, preferably below 3, most preferably below 2.

The electroplating baths of the present invention may be prepared by combining the components in any order. It is preferred that the inorganic components such as metal salts, water, electrolyte, are first added to the bath vessel followed by the organic components such as surfactants, grain refiners, levelers and the like.

Typically, the plating baths of the present invention may be used at any temperature from 10 to 65 degrees C. or higher. It is preferred that the temperature of the plating baths is from 10 to 35 degrees C. and more preferably from 15 degrees to 30 degrees C.

Suitable electrolytes include such as, but not limited to, sulfuric acid, acetic acid, fluoroboric acid, alkylsulfonic acids such as methanesulfonic acid, ethanesulfonic acid, propanesulfonic acid and trifluoromethane sulfonic acid, arylsulfonic acids such as phenyl sulfonic acid and toluenesulfonic acid, sulfamic acid, hydrochloric acid, phosphoric acid, tetraalkylammonium hydroxide, preferably tetramethylammonium hydroxide, sodium hydroxide, potassium hydroxide and the like. Acids are typically present in an amount in the range of from about 1 to about 300 g/l.

In one embodiment the at least one additive comprises a counterion $Y^{o-}$ selected from methane sulfonate, sulfate or acetate. wherein o is a positive integer.

Application

The plating compositions of the present invention are useful in various plating methods where a tin-containing layer is desired, and particularly for depositing a tin-containing solder layer on a semiconductor wafer comprising a plurality of conductive bonding features. Plating methods include, but are not limited to, horizontal or vertical wafer plating, barrel plating, rack plating, high speed plating such as reel-to-reel and jet plating, and rackless plating, and preferably horizontal or vertical wafer plating. A wide variety of substrates may be plated with a tin-containing deposit according to the present invention. Substrates to be plated are conductive and may comprise copper, copper alloys, nickel, nickel alloys, nickel-iron containing materials. Such substrates may be in the form of electronic components such as (a) lead frames, connectors, chip capacitors, chip resistors, and semiconductor packages, (b) plastics such as circuit boards, and (c) semiconductor wafers. Preferably the substrates are semiconductor wafers. Accordingly, the present invention also provides a method of depositing a tin-containing layer on a semiconductor wafer comprising: providing a semiconductor wafer comprising a plurality of conductive bonding features; contacting the semiconductor wafer with the composition described above; and applying sufficient current density to deposit a tin-containing layer on the conductive bonding features. Preferably, the bonding features comprise copper, which may be in the form of a pure copper layer, a copper alloy layer, or any interconnect structure comprising copper. Copper pillars are one preferred conductive bonding feature. Optionally, the copper pillars may comprise a top metal layer, such as a nickel layer. When the conductive bonding features have a top metal layer, then the pure tin solder layer is deposited on the top metal layer of the bonding feature. Conductive bonding features, such as bonding pads, copper pillars, and the like, are well-known in the art, such as described in U.S. Pat. No. 7,781,325, US 2008/0054459 A, US 2008/0296761 A, and US 2006/0094226 A.

Process

In general, when the present invention is used to deposit tin-silver alloys on a substrate the plating baths are agitated during use. Any suitable agitation method may be used with the present invention and such methods are well-known in the art. Suitable agitation methods include, but are not limited to, inert gas or air sparging, work piece agitation, impingement and the like. Such methods are known to those skilled in the art. When the present invention is used to plate an integrated circuit substrate, such as a wafer, the wafer may be rotated such as from 1 to 150 RPM and the plating solution contacts the rotating wafer, such as by pumping or spraying. In the alternative, the wafer need not be rotated where the flow of the plating bath is sufficient to provide the desired metal deposit.

The tin alloy is deposited in recesses according to the present invention without substantially forming voids within the metal deposit. By the term "without substantially forming voids", it is meant that there are no voids in the metal deposit which are bigger than 1000 nm, preferably 500 nm, most preferably 100 nm.

Plating equipment for plating semiconductor substrates are well known. Plating equipment comprises an electroplating tank which holds tin or tin alloy electrolyte and which is made of a suitable material such as plastic or other material inert to the electrolytic plating solution. The tank may be cylindrical, especially for wafer plating. A cathode is horizontally disposed at the upper part of tank and may be any type substrate such as a silicon wafer having openings.

These additives can be used with soluble and insoluble anodes in the presence or absence of a membrane or membranes separating the catholyte from the anolyte.

The cathode substrate and anode are electrically connected by wiring and, respectively, to a power supply. The cathode substrate for direct or pulse current has a net negative charge so that the metal ions in the solution are reduced at the cathode substrate forming plated metal on the cathode surface. An oxidation reaction takes place at the anode. The cathode and anode may be horizontally or vertically disposed in the tank.

In general, when preparing tin alloy bumps, a photoresist layer is applied to a semiconductor wafer, followed by standard photolithographic exposure and development techniques to form a patterned photoresist layer (or plating mask) having openings or vias therein. The dimensions of the plating mask (thickness of the plating mask and the size of the openings in the pattern) defines the size and location of the tin or tin alloy layer deposited over the I/O pad and UBM. The diameter of such deposits typically range from 1 to 300 μm, preferably in the range from 2 to 100 μm.

All percent, ppm or comparable values refer to the weight with respect to the total weight of the respective composition except where otherwise indicated. All cited documents are incorporated herein by reference.

The following examples shall further illustrate the present invention without restricting the scope of this invention.

EXAMPLES

Example 1: Preparation of Complexing Agents

Preparation of Thiols 2-(ethylsulfanyl)ethane-1-thiol

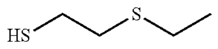

Under inert atmosphere 36.4 g thiourea were added to a solution of 51.8 g 2-ethylthioethanol in 142.2 g of 32% hydrochloric acid. The mixture was stirred at 100° C. for 7.5 h followed by stirring at room temperature overnight. After the addition of 634 ml of 2 M potassium hydroxide solution in water the mixture was refluxed for 3.5 h, cooled to room temperature and acidified with each and the combined organic layers were dried over sodium sulfate. The solvent was removed in vacuo to yield 52.5 g of 2-(ethylsulfanyl) ethane-1-thiol as a colorless liquid.

2-isopropylsulfanylethanethiol

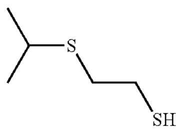

Under inert atmosphere 15.6 g thiourea were added to a solution of 24.6 g 2-isopropylthioethanol in 60.9 g of 32% hydrochloric acid. The mixture was refluxed for 7.5 h followed by stirring at room temperature overnight. After the addition of 272 ml of 2 M potassium hydroxide solution in water the mixture was refluxed for 3.5 h, cooled to room temperature and acidified with hydrochloric acid to pH 1. The mixture was extracted three times with 100 ml dichloromethane each and the combined organic layers were dried over sodium sulfate. The solvent was removed in vacuo to yield 24.7 g of 2-isopropylsulfanylethanethiol as a colorless liquid.

2-benzylsulfanylethanethiol

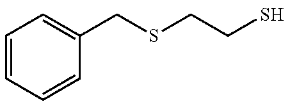 [SMILES: SCCSCc1ccccc1]

11.4 g 2-hydroxyethylbenzylsulfid were dissolved in 20 ml chloroform. A solution of 10.0 g thionylchloride in 30 ml chloroform was added dropwise within 35 min while keeping the temperature between 21 and 29° C. The mixture was stirred at room temperature for 1 h. The solvent was removed in vacuo to yield 12.7 g of 2-chloroethylsulfanylmethylbenzene as a yellow liquid.

12.7 g 2-chloroethylsulfanylmethylbenzene were dissolved in 30 ml ethanol. A solution of 5.16 g thiourea in 50 ml ethanol was added. The mixture was refluxed for 5 h followed by stirring at room temperature overnight. The solvent was removed in vacuo and the residue was mixed with 200 ml dichloromethane. The participate was filtered off and washed with dichloromethane. After drying under air 15.7 g of (2-benzylsulfanylethylsulfanylcarbonimidoyl)ammoniumchloride were obtained as a white powder.

6.0 g (2-benzylsulfanylethylsulfanylcarbonimidoyl)ammoniumchloride were suspendet in 150 ml water. After the addition of 1.5 g sodium hydroxide the mixture was stirred at 100° C. for 45 min. The mixture was cooled to room temperature and acidified to pH 1-2 using hydrochloric acid. The mixture was extracted three times with 30 ml dichloromethane each. The combined organic layers were dried over sodium sulfate. The solvent was removed in vacuo to yield 3.8 g of 2-benzylsulfanylethanethiol as a yellow liquid.

Example 1.1: 3-[2-(2,3-dihydroxypropylsulfanyl)phenyl]sulfanylpropane-1,2-diol

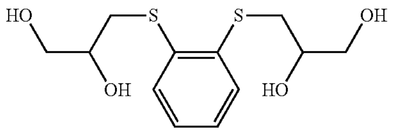

To a solution of 1.81 g 1,2-benzenedithiol in 40 ml dichloromethane were added 0.17 g of potassium carbonate followed by the dropwise addition of 1.88 g glycidol at room temperature. The reaction mixture was stirred at room temperature overnight. After concentration in vacuo the residue was purified by chromatography on silica gel with dichloromethane/methanol as the eluents (elution with a gradient) to yield 2.4 g of 3-[2-(2,3-dihydroxypropylsulfanyl)phenyl]sulfanylpropane-1,2-diol as a colorless oil (assay by C-NMR>95%).

Example 1.2: 3-[2-(2,3-dihydroxypropylsulfanyl)-4-methyl-phenyl]sulfanylpropane-1,2-diol

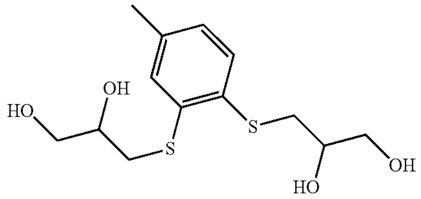 [SMILES: Cc1ccc(SCC(O)CO)c(SCC(O)CO)c1]

To a solution of 1.98 g toluene-3,4-dithiol in 40 ml dichloromethane were added 0.17 g of potassium carbonate followed by the dropwise addition of 1.88 g glycidol at room temperature. The reaction mixture was stirred at room temperature overnight. After concentration in vacuo the residue was purified by chromatography on silica gel with dichloromethane/methanol as the eluents (elution with a gradient) to yield 2.6 g of 3-[2-(2,3-dihydroxypropylsulfanyl)-4-methylphenyl]sulfanylpropane-1,2-diol as a colorless oil (assay by C-NMR 95%).

Example 1.3: 3-[[4-(2,3-dihydroxypropylsulfanylmethyl)phenyl]methylsulfanyl]propane-1,2-diol

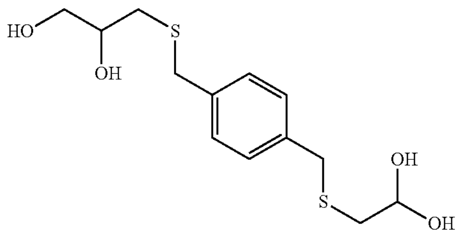 [SMILES: OCC(O)CSCc1ccc(CSCC(O)O)cc1]

Under inert atmosphere 5.9 g of a 30% solution of sodium methylate in methanol were mixed with 30 ml methanol. 3.25 g 3-mercapto-1,2-propanediol were added and the mixture was stirred at room temperature for 30 min. 2.6 g α,α'-dichloro-p-xylene were added and the mixture was stirred at 50° C. for 5.5 h followed by stirring at room temperature overnight. After concentration in vacuo the residue was purified by chromatography on silica gel with dichloromethane/methanol as the eluents (elution with a gradient) to yield 2.0 g of 3-[[4-(2,3-dihydroxypropylsulfanylmethyl)phenyl]methylsulfanyl]propane-1,2-diol as a colorless oil (assay by C-NMR>95%).

Example 1.4: 3-[[3-(2,3-dihydroxypropylsulfanylmethyl)phenyl]methylsulfanyl]propane-1,2-diol

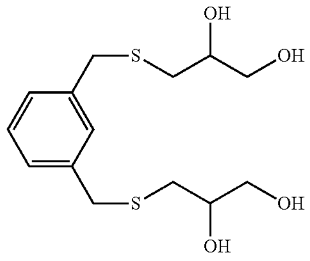 [SMILES: OCC(O)CSCc1cccc(CSCC(O)CO)c1]

To a solution of 2.20 g 1,3-benzenedimethandithiol in 40 ml dichloromethane were added 0.17 g of potassium carbonate followed by the dropwise addition of 1.96 g glycidol at room temperature. The reaction mixture was stirred at room temperature overnight. After concentration in vacuo the residue was purified by chromatography on silica gel with dichloromethane/methanol as the eluents (elution with a gradient) to yield 1.8 g of 3-[[3-(2,3-dihydroxypropylsulfanylmethyl)phenyl]methylsulfanyl]propane-1,2-diol as a white oil (assay by C-NMR 95%).

Example 1.5: 2-[2-(2-hydroxyethylsulfanyl)phenyl]sulfanylethanol

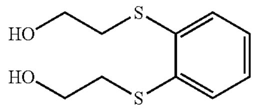 [SMILES: OCCSc1ccccc1SCCO]

To a solution of 2.10 g 1,2-dithiobenzene in 40 ml methanol were added 5.60 g of a 30% solution of sodium methylate in methanol at room temperature. 2.30 of chloroethanol were added and the mixture was stirred at room temperature overnight. 100 ml of water were added, and the mixture was extracted three times with 100 ml methyl tert-butyl ether each. The combined organic layers were washed with 100 ml water and dried over sodium sulfate. After concentration in vacuo the residue was purified by chromatography on silica gel with cyclohexane/ethyl acetate as the eluents (elution with a gradient) to yield 0.7 g of 2-[2-(2-hydroxyethylsulfanyl)phenyl]sulfanylethanol (assay by C-NMR>95%).

Example 1.6: 2-phenylsulfanylethanol

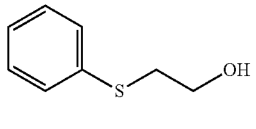

Commercially available: Aldrich, TCI

Example 1.7: 1-(3-hydroxyphenyl)-3-methyl-thiourea

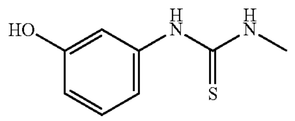

Commercially available: FCH-Group, ZereneX Company

Example 1.8: 2-[2-(2-ethylsulfanylethylsulfanyl)ethyl]pyridine

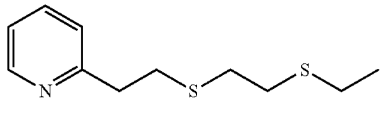

Under inert atmosphere 3.22 g 2-vinylpyridine were dissolved in 30 ml iso-propanol. 3.67 g 2-(ethylsulfanyl)ethane-1-thiol were added and the mixture was refluxed for 7.5 h followed by stirring at room temperature overnight. After concentration in vacuo the residue was purified by chromatography on silica gel with cyclohexane/ethyl acetate as the eluents (elution with a gradient) to yield 5.6 g of 2-[2-(2-ethylsulfanylethylsulfanyl)ethyl]pyridine as a colorless liquid (assay by C-NMR>95%).

Example 1.9: 2,6-bis(2-ethylsulfanylethylsulfanylmethyl)pyridine

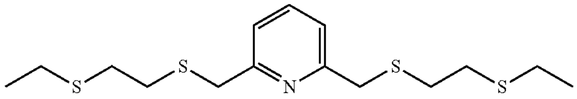 [SMILES: CCSCCSCc1cccc(CSCCSCC)n1]

Under inert atmosphere 3.67 g 2-(ethylsulfanyl)ethane-1-thiol were added to a mixture of 5.94 g of a 30% solution of sodium methylate in methanol and 30 ml methanol. After the addition of 3.97 g 2,6-bis(bromomethyl)pyridine the mixture was stirred at 50° C. for 5.5 h followed by stirring at room temperature overnight. After concentration in vacuo the residue was purified by chromatography on silica gel with cyclohexane/ethyl acetate as the eluents (elution with a gradient) to yield 4.1 g of 2,6-bis(2-ethylsulfanylethylsulfanylmethyl)pyridine as a pale yellow oil (assay by C-NMR 95%).

Example 1.10: 2-(2-ethylsulfanylethylsulfanylmethyl)pyridine

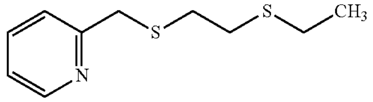

Under inert atmosphere 1.22 g 2 (ethylsulfanyl)ethane-1-thiol were added to a mixture of 7.13 g of a 21% solution of sodium ethylate in ethanol and 15 ml ethanol. A solution of 1.64 g 2-chloromethylpyridine hydrochloride in 15 ml ethanol was added dropwise at 0° C. The mixture was stirred at room temperature overnight. After concentration in vacuo the residue was purified by chromatography on silica gel with cyclohexane/ethyl acetate as the eluents (elution with a gradient) to yield 1.5 g of 2-(2-ethylsulfanylethylsulfanylmethyl)pyridine as a pale yellow liquid (assay by C-NMR 95%).

Example 1.11: 2-(2-pyridylsulfanyl)ethanol

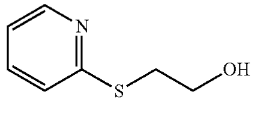

Commercially available, e.g. from Aldrich

Example 1.12: 2-pyrimidin-2-ylsulfanylethanol

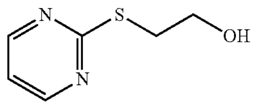

Commercially available: e.g. from Enamine

Example 1.13: 2-[2-(2-isopropylsulfanylethylsulfanyl)ethyl]pyridine

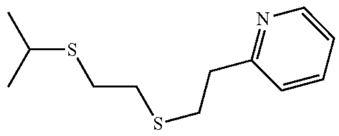

Under inert atmosphere 1.05 g 2-vinylpyridine were added to a solution of 1.36 g 2-isopropylsulfanylethanethiol in 20 ml iso-propanol. The mixture was refluxed for 7.5 h followed by stirring at room temperature overnight. After concentration in vacuo the residue was purified by chromatography on silica gel with cyclohexane/ethyl acetate as the eluents (elution with a gradient) to yield 1.8 g of 2-[2-(2-isopropylsulfanylethylsulfanyl)ethyl]pyridine as a pale yellow liquid (assay by C-NMR 95%).

Example 1.14: 2-(2-ethylsulfanylethylsulfanylmethyl)-6-[6-(2-ethylsulfanylethylsulfanylmethyl)-2-pyridyl]pyridine

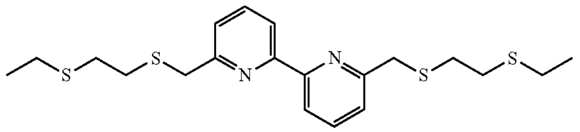 [SMILES: CCSCCSCc1cccc(-c2cccc(CSCCSCC)n2)n1]

Under inert atmosphere 0.97 g 2-(ethylsulfanyl)ethane-1-thiol were added to a mixture of 1.57 g of a 30% solution of sodium methylate in methanol and 20 ml methanol. After the addition of 1.0 g 6,6'-bis(chloromethyl)-2,2'-bipyridine the mixture was stirred at 50° C. for 5.5 h followed by stirring at room temperature overnight. After concentration in vacuo the residue was purified by chromatography on silica gel with cyclohexane/ethyl acetate as the eluents (elution with a gradient) to yield 1.3 g of 2-(2-ethylsulfanylethylsulfanylmethyl)-6-[6-(2-ethylsulfanylethylsulfanylmethyl)-2-pyridyl]pyridine as a yellow liquid (assay by C-NMR 95%).

Example 1.15: 2-[2-(2-benzylsulfanylethylsulfanyl)ethyl]pyridine

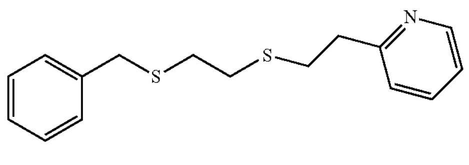 [SMILES: c1ccc(CSCCSCCc2ccccn2)cc1]

Under inert atmosphere 1.05 g 2-vinylpyridine were added to a solution of 1.84 g 2-benzylsulfanylethanethiol in 20 ml iso-propanol. The mixture was refluxed for 4.5 h followed by stirring at room temperature overnight. After concentration in vacuo the residue was purified by chromatography on silica gel with cyclohexane/ethyl acetate as the eluents (elution with a gradient) to yield 2.0 g of 2-[2-(2-benzylsulfanylethylsulfanyl)ethyl]pyridine as a colorless liquid (assay by C-NMR 90%).

Example 1.16: 2-[2-(2-ethylsulfanylethylsulfanyl)-ethyl]pyrazine

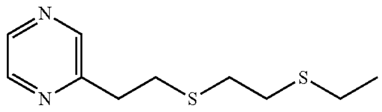

Under inert atmosphere 1.31 g 2 (ethylsulfanyl)ethane-1-thiol were added to a solution of 1.14 g 2 vinylpyrazine in 20 ml iso-propanol. The mixture was refluxed for 6 h followed by the addition of 25 mg azobisisobutyronitrile. The mixture was refluxed for 7 h followed by the addition of another 25 mg azobisisobutyronitrile. The mixture was refluxed for 6 h. After concentration in vacuo the residue was purified by chromatography on silica gel with cyclohexane/ethyl acetate as the eluents (elution with a gradient) to yield 0.11 g of 2-[2-(2-ethylsulfanylethylsulfanyl)ethyl]pyrazine as an orange liquid (assay by C-NMR 95%).

Example 1.17: 3-[[6-[6-(2,3-dihydroxypropylsulfanylmethyl)-2-pyridyl]-2-pyridyl]methylsulfanyl]propane-1,2-diol

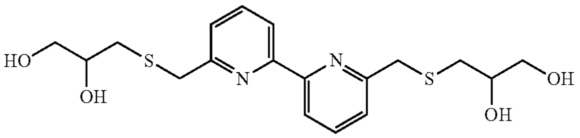 [SMILES: OCC(O)CSCc1cccc(-c2cccc(CSCC(O)CO)n2)n1]

Under inert atmosphere 1.20 g potassium carbonate and 0.86 g 3-mercapto-1,2-propanediol were added to a solution of 1.0 g 6,6'-bis(chloromethyl)-2,2'-bipyridine in 20 ml N,N-dimethylformamide. The mixture was stirred at 80° C. for 7 h followed by stirring at room temperature overnight. Another 0.86 g 3-mercapto-1,2-propanediol were added and the mixture was stirred at 80° C. for 6 h followed by stirring at room temperature over two days. The solvent was removed in vacuo, 10 ml water were added, and the pH was adjusted to 6-7 using hydrochloric acid. 50 ml ethyl acetate were added, and the mixture war extracted three times with 50 ml ethyl acetate each. The combined organic layers were dried over sodium sulfate. After concentration in vacuo the residue was purified by chromatography on silica gel with dichloromethane/methanol as the eluents (elution with a gradient) to yield 1.0 g 3-[[6-[6-(2,3-dihydroxypropylsulfanylmethyl)-2-pyridyl]-2-pyridyl]methylsulfanyl]propane-1,2-diol as a pale yellow powder (assay by C-NMR 95%).

Example 1.18: 2-[2-(2-phenylsulfanylethylsulfanyl)ethyl]pyridine

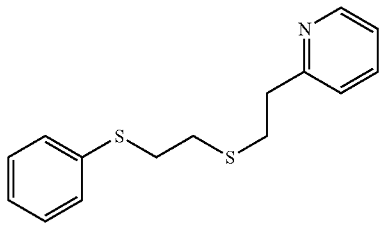 [SMILES: c1ccc(SCCSCCc2ccccn2)cc1]

Under inert atmosphere 1.05 g 2-vinylpyridine were added to a solution of 1.70 g 2-(phenylsulfanyl)ethane-1-thiol in 20 ml iso-propanol. The mixture was refluxed for 4.5 h followed by stirring at room temperature overnight. After concentration in vacuo the residue was purified by chromatography on silica gel with cyclohexane/ethyl acetate as the eluents (elution with a gradient) to yield 2.5 g of 2-[2-(2-phenylsulfanylethylsulfanyl)ethyl]pyridine as a colorless liquid (assay by C-NMR 95%).

Example 1.19: 1-[2-(2-ethylsulfanylethylsulfanyl)ethyl]imidazole

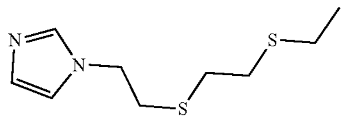

Under inert atmosphere 0.94 g 1-vinylimidazole were dissolved in 20 ml iso-propanol. 1.22 g 2-(ethylsulfanyl)ethane-1-thiol and 25 mg azobisisobutyronitrile were added and the mixture was refluxed for 6.5 h followed by stirring at room temperature over two days. After concentration in vacuo the residue was purified by chromatography on silica gel with cyclohexane/ethyl acetate as the eluents (elution with a gradient) to yield 1.4 g of 1-[2-(2-ethylsulfanylethylsulfanyl)ethyl]imidazole as a pale yellow liquid (assay by C-NMR 90%).

Example 1.20: 2-[2-(2-ethylsulfanylethylsulfanyl)-1-methyl-ethyl]thiazole

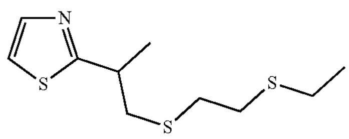

Under inert atmosphere 1.25 g 2-isopropenylthiazole were dissolved in 20 ml iso-propanol. 1.22 g 2-(ethylsulfanyl)ethane-1-thiol were added and the mixture was refluxed for 6.0 h followed by the addition of 25 mg azobisisobutyronitrile. The mixture was refluxed for 7.0 h followed by the addition of another 25 mg azobisisobutyronitrile. The mixture was refluxed for 6.0 h. After concentration in vacuo the residue was purified by chromatography on silica gel with cyclohexane/ethyl acetate as the eluents (elution with a gradient) to yield 0.58 g of 2-[2-(2-ethylsulfanylethylsulfanyl)-1-methyl-ethyl]thiazole as a pale yellow liquid (assay by C-NMR 95%).

Example 1.21: Morpholine-4-carbodithioate, Tetramethylammonium Salt

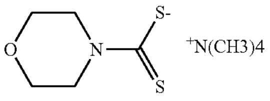

16.4 g morpholine and 38 g tetramethylammonium hydroxide were dissolved at 25° C. under inert atmosphere in 50 g THF. Then the reaction mixture was cooled to 5° C. and 15.2 g $CS_2$ dissolved in 100 ml THF were added over a period of 2 hours. The reaction mixture post-react for 4.5 hours under increasing temperature up to 25° C.The crude product was filtered, washed three times with acetone and dried under vacuo. The final product was obtained as orange crystals to yield 22.5 g (48%).

Example 1.22: Piperazine-1,4-dicarbodithioate, Ditetramethylammonium Salt

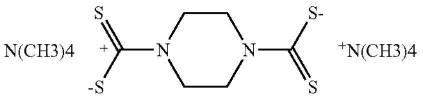

8.6 g piperazine and 38.1 g tetramethylammonium hydroxide were dissolved at 25° C. under inert atmosphere in 60 g methanol. Then the reaction mixture was cooled to 5° C. and 15.2 g $CS_2$ dissolved in 100 ml THF were added over a period of 2 hours. The reaction mixture post-react for 2 hours under increasing temperature up to 25° C. The crude product was filtered, washed three times with acetone and dried under vacuo. The final product was obtained as yellow crystals to yield 22.6 g (59%).

Example 1.23: 4-[2-(2-ethylsulfanylethylsulfanyl)ethyl]morpholine

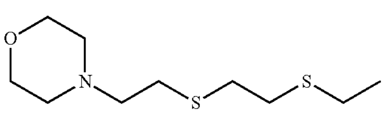

Under inert atmosphere 1.22 g 2-(ethylsulfanyl)ethane-1-thiol were added to a mixture of 7.13 g of a 21% solution of sodium ethylate in ethanol and 10 ml ethanol. The mixture was stirred at room temperature for 15 min. A solution of 1.86 g 4-(2-chloroethyl)morpholine hydrochloride in 15 ml ethanol was added dropwise. The mixture was stirred at room temperature for 96 h. After concentration in vacuo the residue was purified by chromatography on silica gel with cyclohexane/ethyl acetate as the eluents (elution with a gradient) to yield 1.3 g of 4-[2-(2-ethylsulfanylethylsulfanyl)ethyl]morpholine as a pale yellow liquid (assay by C-NMR 95%).

Example 1.24: 1-[2-(2-ethylsulfanylethylsulfanyl)ethyl]pyrrolidin-2-one

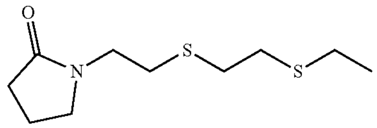

1.11 g 1-vinyl-2-pyrrolidone were dissolved in 30 ml iso-propanol. 1.22 g 2-(ethylsulfanyl)ethane-1-thiol were added and the mixture was refluxed for 7.5 h followed by stirring at room temperature overnight. 25 mg azobisisobutyronitrile were added and the mixture was refluxed for 7.0 h. After concentration in vacuo the residue was purified by chromatography on silica gel with cyclohexane/ethyl acetate as the eluents (elution with a gradient) to yield 1.6 g of 1-[2-(2-ethylsulfanylethylsulfanyl)ethyl]pyrrolidin-2-one as colorless liquid (assay by C-NMR 95%).

Example 2: Stability Test

A silver methanesulfonic acid solution was added to the complexing agent (ratio complexing agent:Ag=10:1). If the complexing agent was insoluble, 2-3 drops of methanesulfonic acid were added. Next, a tin methanesulfonic acid solution containing 4-methoxyphenol (MeHQ) as antioxidant was added. The mixture was then stored at 50° C. for 7 days. If a precipitate was formed, the complexing agent failed the test. If the mixture stayed clear over a period of 3 days, this was an indication for a good complexation ("o"), if the mixture stayed clear over a period of 7 days for a very good complexation ("+").

Assumed that the reaction rate at temperatures<100° C. is tripled when the temperature is increased by 10° C., 7 days at 50° C. should reflect the stability of 6 months at 20° C.

The complexing agents of example 1 were subjected to the test procedure described above. The results are listed in Table 1.

TABLE 1

| No. 1.x | Strukture | Test Results |
|---|---|---|
| 1 | 3-[2-(2,3-dihydroxypropylsulfanyl)phenyl]sulfanylpropane-1,2-diol | + |
| 2 | 3-[2-(2,3-dihydroxypropylsulfanyl)-4-methyl-phenyl]sulfanylpropane-1,2-diol | + |
| 3 | 3-[[4-(2,3-dihydroxypropylsulfanylmethyl)phenyl]methylsulfanyl]-propane-1,2-diol | + |
| 4 | 3-[[3-(2,3-dihydroxypropylsulfanylmethyl)phenyl]methylsulfanyl]-propane-1,2-diol | + |
| 5 | 2-[2-(2-hydroxyethylsulfanyl)phenyl]sulfanylethanol | + |
| 6 | 2-phenylsulfanylethanol | + |
| 7 | 1-(3-hydroxyphenyl)-3-methyl-thiourea | + |
| 8 | 2-[2-(2-ethylsulfanylethylsulfanyl)ethyl]pyridine | + |
| 9 | 2,6-bis(2-ethylsulfanylethylsulfanylmethyl)pyridine | + |
| 10 | 2-(2-ethylsulfanylethylsulfanylmethyl)pyridine | + |
| 11 | 2-(2-pyridylsulfanyl)ethanol | + |
| 12 | 2-pyrimidin-2-ylsulfanylethanol | + |
| 13 | 2-[2-(2-isopropylsulfanylethylsulfanyl)ethyl]pyridine | + |
| 14 | 2-(2-ethylsulfanylethylsulfanylmethyl)-6-[6-(2-ethylsulfanylethyl-sulfanylmethyl)-2-pyridyl]pyridine | + |
| 15 | 2-[2-(2-benzylsulfanylethylsulfanyl)ethyl]pyridine | + |
| 16 | 2-[2-(2-ethylsulfanylethylsulfanyl)-ethyl]pyrazine | ○ |
| 17 | 3-[[6-[6-(2,3-dihydroxypropylsulfanylmethyl)-2-pyridyl]-2-pyridyl]-methylsulfanyl]propane-1,2-diol | ○ |

TABLE 1-continued

| No. 1.x | Strukture | Test Results |
|---|---|---|
| 18 | 2-[2-(2-phenylsulfanylethylsulfanyl)ethyl]pyridine | + |
| 19 | 1-[2-(2-ethylsulfanylethylsulfanyl)ethyl]imidazole | + |
| 20 | 2-[2-(2-ethylsulfanylethylsulfanyl)-1-methyl-ethyl]thiazole | + |
| 21 | Morpholine-4-carbodithioate tetramethylammonium salt | + |
| 22 | Piperazine-1,4-dicarbodithioate, ditetramethylammonium salt | + |
| 23 | 4-[2-(2-ethylsulfanylethylsulfanyl)ethyl]morpholine | + |
| 24 | 1-[2-(2-ethylsulfanylethylsulfanyl)ethyl]pyrrolidin-2-one | + |

Example 3: Electroplating Experiments

The patterned photoresist contained vias of 8 μm diameter and 15 μm depth and pre-formed copper p-bump of 5 μm height. The isolated (iso)-area consists of a 3×6 array of pillars with a center to center distance (pitch) of 32 μm. The dense area consists of an 8×16 array of pillars with a center to center distance (pitch) of 16 μm. For the calculation of the within die coplanarity 3 bumps of the iso-area and 3 bumps from the center of the dense area are taken.

The morphology (roughness) was qualitatively determined by scanning electron microscopy (SEM).

Example 3.1

A tin silver plating bath with the following composition was prepared: 75 g/l tin as tin methanesulfonate, 165 g/l methanesulfonic acid, 0.5 g/l silver as silver methanesulfonate, 5.1 g/l of Mercaptopyridine as Ag complexing agent, 2 g/l of a commercial anti-oxidant and 2 g/l of surfactant 7. 37 μm of a tin silver alloy (SnAg) with a silver content of 1.5% by weight was electroplated on a copper bump. The copper bump had a diameter of 50 μm and a height of 5 μm. A 2 cm×2 cm large wafer coupon with a 70 μm thick patterned photo resist layer was immersed in the above described plating bath and a direct current of 6 ASD (=60 mA/cm 2) has been applied for 814 s at 25° C.

The plated tin silver bump was examined by scanning electron microscopy (SEM). The SEM image is shown in FIG. 1. The qualitative morphology assessment is summarized in Table 2.

Example 3.2

A tin silver plating bath with the following composition was prepared: 75 g/l tin as tin methanesulfonate, 165 g/l methanesulfonic acid, 0.5 g/l silver as silver methanesulfonate, 5.1 g/l of 3-[2-(2,3-dihydroxypropylsulfanyl)phenyl]sulfanylpropane-1,2-diol of Example 1.1 as Ag complexing agent, 2 g/l of a commercial anti-oxidant and 2 g/l of surfactant 7. 37 μm of a tin silver alloy (SnAg) with a silver content of 1.5% by weight was electroplated on a copper bump. The copper bump had a diameter of 50 μm and a height of 5 μm. A 2 cm×2 cm large wafer coupon with a 70 μm thick patterned photo resist layer was immersed in the above described plating bath and a direct current of 6 ASD has been applied for 814 s at 25° C.

The plated tin silver bump was examined by scanning electron microscopy (SEM). The qualitative morphology assessment is summarized in Table 2.

Example 3.3

A tin silver plating bath with the following composition was prepared: 75 g/l tin as tin methanesulfonate, 165 g/l methanesulfonic acid, 0.5 g/l silver as silver methanesulfonate, 5.1 g/l of 3-[2-(2,3-dihydroxypropylsulfanyl)phenyl]sulfanylpropane-1,2-diol of Example 1.6 as Ag complexing agent, 2 g/l of a commercial anti-oxidant and 2 g/l of surfactant 7. 37 μm of a tin silver alloy (SnAg) with a silver content of 1.5% by weight was electroplated on a copper bump. The copper bump had a diameter of 50 μm and a height of 5 μm. A 2 cm×2 cm large wafer coupon with a 70 μm thick patterned photo resist layer was immersed in the above described plating bath and a direct current of 6 ASD has been applied for 814 s at 25° C.

The plated tin silver bump was examined with scanning electron microscopy (SEM). The qualitative morphology assessment is summarized in Table 2.

TABLE 2

| Example | Structure | Morphology |
|---|---|---|
| C 3.1 | Mercaptopyridine (Prior Art) | Very rough |
| 3.2 | 3-[2-(2,3-dihydroxypropylsulfanyl) phenyl]sulfanylpropane-1,2-diol | Smooth |
| 3.3 | 2-phenylsulfanylethanol | Smooth |

Table 2 shows that the thioether compounds of examples 3.2 (compound 1.1) and 3.3 (compound 1.6) according to the invention show a much better morphology compared to the thiol compound of comparative example $C_{3.1.}$

The invention claimed is:

1. An aqueous composition comprising (a) metal ions comprising tin ions and silver ions and (b) at least one complexing agent of formula C11

$R^{C12}$-$X^{C11}$- $R^{C11}$ (C11)

and their salts, wherein $X^{C11}$ is selected from the group consisting of
- (a) a divalent 5 or 6 membered aromatic N-heterocyclic group comprising
  - (i) a single N atom; or
  - (ii) a first N atom and a second heteroatom selected from N and S, wherein the first N atom and the second heteroatom are separated by at least one C atom; or
  - (iii) a triazole or a thiadiazole;
- (b) a divalent 6 membered aromatic carbocyclic group; and
- (c) a divalent 5 or 6 membered aliphatic N-heterocyclic group comprising one N atom and optionally a second heteroatom selected from the group consisting of N and O;

all of which may be unsubstituted or substituted by one or more OH or one or more $R^{C14}$;

$R^{C11}$ is selected from the group consisting of (a) -$X^{C12}$-S[-$X^{C13}$-$D^{C11}$]$_n$-$R^{C13}$, (b)

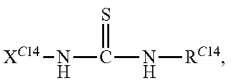

and (c)

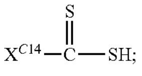

$R^{C12}$ is selected from the group consisting of $R^{C11}$, $X^{C11}$-$R^{C11}$, H, OH, $C_1$ to $C_{10}$ alkyl, and $C_1$ to $C_{10}$ alkoxy, with the proviso that if $X^{C11}$ is a divalent 6 membered aromatic carbocyclic group, then $R^{C12}$ is selected from the group consisting of $R^{C11}$, $X^{C11}$-$R^{C11}$, $C_1$ to $C_{10}$ alkyl, and $C_1$ to $C_{10}$ alkoxy;

$X^{C12}$ is a chemical bond or a linear, branched or cyclic $C_1$-$C_6$ alkanediyl, which may be unsubstituted or substituted by OH, with the proviso that if (a) $X^{C11}$ is a divalent 5 or 6 membered aromatic N-heterocyclic group and (b) $R^{C13}$ is substituted by one OH and (c) $R^{C12}$ is not $R^{C11}$, then $X^{C12}$ is a chemical bond;

$X^{C13}$ is a linear, branched or cyclic $C_1$-$C_6$ alkanediyl, which may be unsubstituted or substituted by OH;

$X^{C14}$ is a chemical bond or a linear or branched $C_1$-$C_4$ alkanediyl;

$D^{C11}$ is selected from the group consisting of S and O;

$R^{C13}$ is selected from the group consisting of (a) a linear, branched or cyclic $C_1$-$C_6$ alkyl, which may be unsubstituted or substituted by one or more OH, (b) Ph or $X^{C14}$-Ph, which may be substituted by OH or $R^{C14}$, with Ph=phenyl, when $X^{C11}$ is not the aromatic carbocyclic group, and (c) a $C_2$ to $C_4$ polyoxyalkylene group;

with the proviso that if $X^{C11}$ is a divalent 5 or 6 membered aromatic N- heterocyclic group, then $R^{C13}$ is unsubstituted or substituted by one OH with the exception that if $X^{C11}$ is a divalent 5 or 6 membered aromatic N-heterocyclic group comprising a first N atom and a second heteroatom that is N, then $R^{C13}$ is unsubstituted;

$R^{C14}$ is selected from the group consisting of H and a linear, branched or cyclic $C_1$-$C_6$ alkyl; and n is 0 or an integer of from 1 to 5;

wherein the composition is free of copper ions.

2. The aqueous composition according to claim 1, wherein $R^{C11}$ is -$X^{C12}$—S[$X^{C13}$-$D^{C11}$]$_n$-$R^{C13}$.

3. The aqueous composition according to claim 2, wherein $X^{C12}$ is a linear or branched $C_1$-$C_4$ alkanediyl, which may be unsubstituted or substituted by OH, with the proviso that if (a) $X^{C11}$ is a divalent 5 or 6 membered aromatic N-heterocyclic group and (b) $R^{C13}$ is substituted by one OH and (c) $R^{C12}$ is not $R^{C12}$, then $X^{C12}$ is a chemical bond.

4. The aqueous composition according to claim 2, wherein n is 1 or 2; $D^{C11}$ is S; and $X^{C13}$ is a linear or branched $C_1$-$C_4$ alkanediyl, which may be unsubstituted or substituted by one or more OH.

5. The aqueous composition according to claim 2, wherein $R^{C13}$ is selected from the group consisting of (a) a linear or branched $C_1$-$C_4$ alkyl, which may be unsubstituted or substituted by one or more OH, (b) phenyl or benzyl, which may be substituted by OH, methyl or ethyl, where $X^{C11}$ is not the aromatic carbocyclic group, and (c) a polyoxyethylene or a poly(oxyethylene-co-oxypropylene), with the proviso that if $X^{C11}$ is a divalent 5 or 6 membered aromatic N-heterocyclic group, then $R^{C13}$ is unsubstituted or substituted by one OH with the exception that if $X^{C11}$ is a divalent 5 or 6 membered aromatic N-heterocyclic group comprising a first N atom and a second heteroatom selected from the group consisting of N, then $R^{C13}$ is unsubstituted.

6. The aqueous composition according to claim 2, wherein n is 0 or 1.

7. The aqueous composition according to claim 2, wherein n is 1; $D^{C11}$ is S; and $X^{C13}$ is a linear or branched $C_1$-$C_4$ alkanediyl, which may be unsubstituted or substituted by one or more OH.

8. The aqueous composition according to claim 1, wherein $R^{C11}$ is

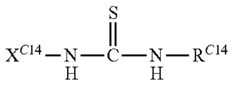

or

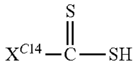

wherein $X^{C14}$ is a chemical bond, methanediyl, ethanediyl, or propanediyl; and $R^{C14}$ is H, methyl, ethyl or propyl.

9. The aqueous composition according to claim 1, wherein $X^{C11}$ is selected from the group consisting of a pyrrole, a pyridine, an imidazole, a pyrimidine, and a thiazole, which may be unsubstituted or substituted by one or more methyl, ethyl or propyl.

10. The aqueous composition according to claim 1, wherein $X^{C11}$ is selected from the group consisting of phenyl, which may be unsubstituted or substituted by one or more methyl, ethyl or propyl.

11. The aqueous composition according to claim 1, wherein $X^{C11}$ is selected from the group consisting of piperidine, piperazine, pyrrolidinone and morpholine, which may be unsubstituted or substituted by one or more methyl, ethyl or propyl.

12. The aqueous composition according to claim 1, wherein $R^{C12}$ is selected from the group consisting of $R^{C11}$ and $X^{C11}$-$R^{C11}$.

13. A process for electrodepositing tin or a tin silver alloy onto a substrate by a) contacting the composition according to claim 1 with the substrate, and b) applying a current to the substrate for a time sufficient to electrodeposit the tin silver alloy layer onto the substrate, wherein the substrate comprises features having an aperture size from 500 nm to 500 μm and the electrodeposition is performed to fill these features.

14. The process according to claim 13, wherein the aperture size is from 1 μm to 200 μm.

* * * * *